US005717071A

United States Patent [19]
Raff

[11] Patent Number: 5,717,071
[45] Date of Patent: Feb. 10, 1998

[54] CROSS-PROTECTIVE HUMAN MONOCLONAL ANTIBODY COMPOSITIONS

[75] Inventor: Howard V. Raff, Seattle, Wash.

[73] Assignee: Bristol-Myers Squibb Company, New York, N.Y.

[21] Appl. No.: 300,118

[22] Filed: Sep. 2, 1994

Related U.S. Application Data

[63] Continuation of Ser. No. 58,987, May 5, 1993, abandoned, which is a continuation of Ser. No. 785,184, Oct. 31, 1991, abandoned, which is a continuation of Ser. No. 944,495, Dec. 19, 1986, abandoned, which is a continuation-in-part of Ser. No. 828,005, Feb. 7, 1986, abandoned.

[51] Int. Cl.$^6$ ............ C07K 6/18; C07K 16/12; C12N 5/22; A61K 39/40
[52] U.S. Cl. ............ 530/387.5; 530/387.1; 530/388.1; 530/388.15; 530/388.4; 424/142.1; 424/137.1; 424/150.1; 435/329; 435/340
[58] Field of Search ............ 530/387.1, 388.4, 530/391.1, 391.7, 387.5, 388.1, 388.15; 435/240.27, 329, 340; 424/150.1, 163.1, 142.1, 137.1

[56] References Cited

U.S. PATENT DOCUMENTS

| | | | |
|---|---|---|---|
| 4,464,465 | 8/1984 | Lostrom | 435/68 |
| 4,587,121 | 5/1986 | Collins et al. | 424/87 |
| 4,675,287 | 6/1987 | Reisfeld et al. | 435/7 |
| 4,677,070 | 6/1987 | Larrick et al. | 435/240 |
| 4,734,279 | 3/1988 | Stephan et al. | 424/85 |
| 4,772,464 | 9/1988 | Rutherford . | |
| 4,777,136 | 10/1988 | Young . | |
| 4,834,975 | 5/1989 | Siadak et al. | 424/87 |
| 5,378,812 | 1/1995 | Siadak et al. | 530/388.4 |

FOREIGN PATENT DOCUMENTS

| | | |
|---|---|---|
| 0105804 | 4/1984 | European Pat. Off. . |
| 0163493 | 5/1985 | European Pat. Off. ......... 435/68 |
| 8501659 | 4/1985 | WIPO . |

OTHER PUBLICATIONS

Moreno, C. et al."Immunological Properties of Monoclonal Antibodies Specific for Meningococcal Polysaccharides: the Protective Capacity of IgM Antibodies Specific for Polysaccharide Group B," *J. Gen. Microbiol.* 129:2451–2456, 1983.
Hiernaux, J.R. et al. "Study of the Idiotypy of Lipopoly-saccharide-specific Polyclonal and Monoclonal Antibodies," *Eur. J. Immunol.* 12:797–803, 1982.
Pluschke, G. et al. "Sodium Dodecyl Sulphate–Polyacrylamide Gel Electrophoresis and Monoclonal Antibodies as Tools for the Subgrouping of *Escherichia coli* Lipopdysaccharide 018 and 023 Antigens," *Infection and Immunity* 51(1):286–293, Jan. 1986.
Sorensen, R.U. et al. "Defective Cellular Immunity to Gram–Negative Bacteria in Cystic Fibrosis Patients," *Infection and Immunity* 23:398–402, Feb. 1979.
Sugasawara, R.J. et al. "Monoclonal Antibodies Against *Neisseria meningitidis* Lipopolysaccharide" *Infection and Immunity* 43(3):863–868, Dec. 1983.
Egan, M.L.,et al., 1983, *J. Exp. Med.*, 1:1006–1011.
Mayer, et al., 1985, *Meths. Microbiology*, 18:157–201.
Sakulramrung and Domingue, 1985, *J. Infect. Dis.*, 151:995–1104.
McCabe, et al., 1977, *J. Infect. Dis.*, 136S:161–166.
Mullan, et a., 1974, *Infect. Immun.*, 10:1195–1201.
Elkins and Metcalf, 1985, *Infect. Immun.* 48:597–600.
Gigliotti and Shenep, 1985, *J. Infect. Dis.* 151:1005–1011.
U.S.S.N. 807,364, 1985,pp. 1–36.
Gigliotti and Shenep, 1985, *J. Infect. Dis.*, 122:100–103.
Frosch, M., et al., 1985, *Proc. Natl. Acad. Sci. USA*, 82:1194–1198.
Guerina, et al., 1983, *J. Infect. Dis.*, 148:395–405.
Zollinger, et al., 1983, *Infect. Immun.* 40:257–264.
Abraham, et al., 1985, *Infect. Immun.* 48:625–628.
Collins, et al., 1984, *Am. J. Med.* 76:155–160.
Teng, et al., 1985, *Proc. Natl. Acad. Sci. U.S.A.* 82:1790–1794.
Hornberger, et al., 1985, *Fed. AM. Soc. Exp. Biol.*, 69th Ann. Meet., Abst. No. 5366.
Kirkland, et al., 1984, *J. Immunol.* 132:2590–2592.
Cryz, et al., 1984, *Infect. Immun.* 45:139–142.
Gigliotti, et al., 1984, *J. Infect. Dis.* 149:43–47.
Hunter, Jr., et al., 1984, *New Horiz. Microbiology*, pp. 99–106.
Artenstein, et al., 1975, New Approaches for Inducing Natural Immunity to Pyogenic Organisms, pp. 57–58.
Robbins, et al., 1975, New Approaches for Inducing Natural Natural Immunity to Pyogenic Organisms, pp. 59–62.
Givner, et al., 1985, *J. Infect. Dis.* 151:217–220.
Ruch, Jr., et al., 1982, *J. Clin. Microbiol.* 16:145–152.
Baltimore, et al., 1979, *J. Infect. Dis.* 140:81–88.
Finne, et al., 1983, *Lancet* 2:355–357.

(List continued on next page.)

*Primary Examiner*—Susan A. Loring
*Attorney, Agent, or Firm*—Townsend and Townsend and Crew LLP

[57] ABSTRACT

Cell lines have been produced that secrete human monoclonal antibodies capable of binding to molecules of different bacterial species. These antibodies have been found to be protective against lethal challenges of various bacterial genera. Pharmaceutical compositions containing these antibodies, which can be in combination with other monoclonal antibodies, blood plasma fractions and antimicrobial agents, and the prophylactic and therapeutic use of such compositions in the management of infections are included. Prior to filing of this patent application the continuous transformed human cell lines 9B10, 4F10, 4B9, 7D7, and 9C3, described herein, were deposited in the American Type Culture Collection and given the designations CRL 9006, CRL 9007, CRL 9008, CRL 9009, and CRL 9239, respectively.

23 Claims, No Drawings

OTHER PUBLICATIONS

Kasper, et al., 1973, *J. Immunol.* 110:262–268.

Verhoef, et al., Eur. J. Clin Microbiol. Infect. Dis, 9(4):247–250, Apr. 1990.

Ceriani, R.L. et al., Proceedings of the Int. Workshop on Monoclonal Antibodies & Breast Cancer, pp. 248–268, Nov. 8–9, 1984.

Spalding, B.J., Bio/Technology, 11:428–429, Apr. 1993.

Stone, R., Science, 259:1243, 26 Feb. 1993.

Fitzer–Schiller, G., The Washington Post, D3, Jan. 19, 1993.

Harris, W.J., et al, TiBTECH, 11:42–44, 1993.

Waldmam, T.A., Science, 252:1657–1662, Jun. 1991.

Osband, M.E. et al., Immunology Today, 11(6):193–195, 1990.

Wilkinson, S.G., "Surface Carbohydrates of the Probaryotic Cell", pub. Academic Press Inc, pp. 97–171, 1977.

Cross, A.S., et al., 1983, *J. Infect. Dis.*, 147:68–76.

Soderstrom, T., et al., 1983, *Prog. Allergy* 33:259–274.

Cross, A.S., et al., 1984, *J. Infect. Dis.*, 149:184–193.

CROSS-PROTECTIVE HUMAN MONOCLONAL ANTIBODY COMPOSITIONS

This is a continuation of Ser. No. 08/058,987, filed May 5, 1993, now abandoned, which is a continuation of Ser. No. 07/785,184, filed Oct. 31, 1991, now abandoned, which is a continuation of Ser. No. 06/944,495, filed Dec. 19, 1986, now abandoned, which is a continuation-in-part of Ser. No. 06/828,005, filed Feb. 7, 1986, now abandoned.

FIELD OF THE INVENTION

The present invention relates to the application of immunological techniques to provide novel materials useful in treating and diagnosing bacterial infections and, more particularly, to the production and application of human monoclonal antibodies that are capable of protecting against infections caused by different genera of bacteria.

BACKGROUND OF THE INVENTION

Gram-positive and gram-negative bacteria may cause life-threatening disease in infected patients. These bacterial infections often cause significant morbidity and mortality. There is an increased incidence of such infections in prematurely born infants, elderly patients, and patients who have serious underlying medical conditions such as burns, surgical trauma, slow-healing wounds, or malignancies. These infections are typically of nosocomial origin (i.e., hospital-acquired), and occur particularly in patients who have sustained prolonged hospitalization associated with surgical intervention, intravascular insult, or long-term therapy with immunosuppressive agents or antibiotics. In addition, newborns who have an immature immune system are apparently acutely susceptible to neonatal sepsis and meningitis caused by particular gram-negative and gram-positive bacteria.

Included among the most frequently encountered organisms in gram-negative and gram-positive disease are *Escherichia coli* (*E. coli*), *Klebsiella pneumoniae* (*K. pneumoniae*), *Serratia marcescens* (*S. marcescens*), *Enterobacter aerogenes* and *cloacae* (*E. aerogenes/cloacae*), *Pseudomonas aeruginosa* (*P. aeruginosa*), *Neisseria meningitidis* (*N. meningitidis*), Group B Streptococcus and *Staphylococcus aureus* (*S. aureus*) (Sonnenwirth, A. C., "The Enteric Bacilli and Similar Gram-Negative Bacteria," pp. 753–790, in Micro-biology, 2nd Edition, Davis, B. D., Dulbecco, R., Eisen, H. N., Ginserberg, H. S., Wood, W. B., and McCarty, M., Eds., Harper and Row, (1973); McCabe, W. R.., "Gram-Negative Bacteremia," Adv. Intern. Med., 19:135–138 (1974); Kreger, et al., "Gram-Negative Bacteremia III. Reassessment of Etiology, Epidemiology, and Ecology in 612 Patients," Am. J. Med. 68:332–343 (1980); Robbins, J. B., et al., "*Escherichia coli* K1 Capsular Polysaccharide Associated With Neonatal Meningitis," New Engl J. Med., 290:1216–1220 (1974); and Hughs, J. M., et al., "Nosocomial Infection Surveillance, 1980–1982," Morb. Mort. Weekly Report, 32:1SS-16SS (1983)). Of these infections, usually several, but not all, serotypes of certain gram-negative bacteria, e.g., *E. coli*, *K. pneumoniae*, *E. aerogenes/cloacae*, *P. aeruginosa*, and *S. marcescens*, cause bacteremia among the adult population. In contrast to adults, the immunologically immature neonate is particularly susceptible to septicemia and meningitis caused by the encapsulated strains of *E. coli*, *N. meningitidis* Group B, *Hemophilus influenzae* type B, and the five type strains of Group B Streptococcus. Although other bacteria may also cause these infections, the bacteria cited above are the predominant isolates from the aforementioned blood infections.

Antibiotics have long been the primary therapeutic tool for the control and eradication of gram-positive and gram-negative infections. However, the continued incidence and severity of the infections, the continual emergence of antibiotic resistant bacterial strains, and the inherent toxicity of some antibiotics, point to the limitations of antibiotic therapy. These observations have prompted the search for alternative prophylactic and therapeutic approaches.

It is widely believed that antibodies reactive with structures accessible (externally exposed) on live bacteria may facilitate bacterial destruction by any of several mechanisms. Included among these mechanisms are: (1) direct lysis of the bacteria in the presence of serum complement, (2) bacteriostasis, by the blockading of nutrient scavenger receptors, (3) opsonization and subsequent phagocytosis of the bacteria in the presence or absence of serum complement, or (4) prevention of attachment of the bacteria to host tissues (Mims, C. A.. "Recovery from Infection," in *The Pathogenesis of Infectious Disease*, pp. 198–222, Mims, C. A., Ed., Academic Press (1982)). For bacteria that possess surface carbohydrate molecules, such as lipopolysaccharide (LPS) and/or capsules, antibody appears to be most effective via opsonization mechanisms (Kaijser, B., et al., "The Protective Effect Against *E. coli* of O and K Antibodies of Different Immunoglobulin Classes," Scand. J. Immunol., 1:276 (1972)). Therefore, antibodies directed to these accessible carbohydrate structures may provide an effective means for bacterial elimination.

In general, mammals that are exposed to disease-producing bacteria produce antibodies that are specific for LPS or capsule. These antigens are chemically diverse structures composed of frequently repeating oligosaccharide molecules and whose presence determines the serotype of bacterial strains. Since they are often the immunodominant bacterial antigens, serotype specific antibodies (anti-LPS or capsule) have been the most studied of potentially therapeutic antibodies. However, because of the limited cross-reactivity of these antibodies, and the apparent highly diverse nature of carbohydrate antigens on pathogenic gram-positive and gram-negative bacteria, it would be extremely difficult and costly to produce a therapeutic formulation containing only serotype specific antibodies (see, e.g., Kaijser, B. and Ahlstedt, S., "Protective Capacity of Antibodies Against *Escherichia coli* O and K Antigens," Infect. Immun., 17:286–292 (1977); and Morrison, D. C. and Ryan, J. L., "Bacterial Endotoxins and Host Immune Response, "Adv. Immunol , 28:293–450 (1979)). Regardless, various reports have stimulated visions that immunotherapeutic approaches could be found to treat gram-negative bacterial disease.

Fractionated human plasma, enriched for immune globulins containing specific and protective antibodies against the infecting organisms, have been somewhat effective against *P. aeruginosa* infections. (Collins, M. S. and Robey, R. E., "Protective Activity of an Intravenous Immune Globulin (Human) Enriched in Antibody Against Lipopolysaccharide Antigens of *Pseudomonas aeruginosa*, " Amer. J Med., 3:168–174 (1984)). However, commercial products are not yet readily available due to certain inherent limitations which have prevented their widespread use in the treatment of life-threatening bacterial disease.

One such limitation associated with immune globulin compositions is that they are assembled from large pools of plasma samples that have been preselected for the presence of a limited number of particular antibodies. Typically, these pools consist of samples from a thousand donors who may have low titers to some pathogenic bacteria. Thus, at best, there is only a modest increase in the resultant titer of desired antibodies.

Another such limitation is that the preselection process itself requires very expensive, continuous screening of the donor population to assure product consistency. Despite considerable effort, product lots can still vary between batches and geographic regions.

Yet another such limitation inherent in immune globulin compositions is that their use results in coincident administration of large quantities of extraneous proteinaceous substances (e.g., viruses) having the potential to cause adverse biologic effects. The combination of low titers of desired antibodies and high content of extraneous substances often limits, to suboptimal levels, the amount of specific and thus beneficial immune globulin(s) administrable to the patient.

In 1975, Kohler and Milstein reported that certain mouse cell lines could be fused with mouse spleen cells to create hybridomas which would secrete pure "monoclonal" antibodies (Kohler, G. and Milstein, C., "Continuous Cultures of Fused Cells Secreting Anti-body of Predefined Specificity," Nature, 256:495–497 (1975)). With the advent of this technology, the potential existed to produce murine antibodies to any particular determinant or determinants on antigens.

Using this technology, mouse monoclonal antibodies have been derived from mice immunized with polysaccharide from *Neisseria meningitidis* Group B. These murine IgM monoclonal antibodies were observed to bind and opsonize several K1-positive *E. coli* strains regardless of their LPS serotypes (Cross, "Evaluation of Immunotherapeutic Approaches for the Potential Treatment of Infections Caused by K2-Positive *Escherichia coli*," J. Infect. Dis. 147:68–76 (1983), Soderstrom, "Serologial and Functional Properties of Monoclonal Antibodies to *Escherichia coli* Type I Pilus and Capsular Antigens," Prog. Allergy 33:259–274 (1983), and Cross, A. S., et al., "The Importance of the K1 Capsule in Invasive Infections Caused by *Escherichia coli*," J. Inf. Dis., 149:184–193 (1984)). Moreover, the monoclonal antibodies were protective in mice against lethal challenges with *E. coli* K1 and Group B meningococcal organisms (Cross, J. Infect. Dis. 147:68–76 (1983), and Soderstrom, supra). In another example, mouse monoclonal antibodies specific to type III Group B Streptococcus were reported to be protective in a mouse experimental infection model (Egan, M. L., et al., "Protection of Mice from Experimental Infection with Type III Group B Streptococcus Using Monoclonal Antibodies," J. Exp. Med., 1:1006–1011 (1983)).

A mouse monoclonal antibody, while useful in treating mice, has major disadvantages for use in humans. The human immune system is capable of recognizing any mouse monoclonal antibody as a foreign protein. This can result in accelerated clearance of the antibody and thus abrogation of its pharmacological effect (Levy, R. and Miller, R. A., "Tumor Therapy with Monoclonal Antibodies," Fed. Proc., 42:2650–2656 (1983)). More seriously, this could conceivably lead to shock and even death from allergic reactions analogous to "serum sickness." Clinical experience has shown that anti-mouse immunoglobulin responses have limited the utility of these antibodies in approximately one-half of the patients receiving mouse monoclonal antibodies for treatment of various tumors (Sears, H. F., et al., "Phase I Clinical Trial of Monoclonal Antibody in Treatment of Gastrointestinal Tumor," Lancet, 1:762–764 (1982); and Miller, R. A., et al., "Monoclonal Antibody Therapeutic Trials in Seven Patients with T-Cell Lymphoma," Blood, 62:988–995 (1983)).

Accordingly, there is a need for human monoclonal antibodies which are protective against gram-negative and gram-positive bacterial disease. However, the diverse antigenicity of gram-positive and gram-negative disease-causing bacteria strongly suggests that producing serotype specific human monoclonal antibodies to each of the many important bacterial pathogens would be impractical.

The diverse antigenicity of gram-negative bacteria is attributed to the variable regions of the lipopolysaccharide (LPS), a molecule associated with the outer membrane of gram-negative organisms. The LPS molecule is generally considered to be composed of three structural regions. The region closest to the outer membrane is the so-called lipid A portion of LPS. This structurally conserved region possesses the endotoxic activity associated with gram-negative disease. The second structural region, termed core, is linked to a lipid A often via a 2-keto-3-deoxy-D-mannooctonate residue (KDO) and, similar to the lipid A region, is not usually accessible to antibody when the third outermost region of LPS is present. Although this region is partially conserved within some gram-negative bacterial species, many deviations in complete core have been found among members of the family Enterobacteriaceae. The outermost region of an LPS molecule is composed of repeating oligosaccharide units and is known as the O-specific side chain. The sugars in these oligosaccharide units comprise molecular entities that exhibit serotype specific structural antigenic diversity. Thus, the sugars themselves, their sequence, and their linkages determine O-side chain antigenicity via their tertiary structure. Antibodies to these O-groups have generally been found to be serotype specific. Serotypes are typically defined by their reactivity with monospecific antisera, which possess binding activity for only one particular antigenic determinant. See generally, Mayer et al., Meths. Microbiology, 18:157–201 (1985).

Antisera to the core and lipid A regions of LPS have been produced in efforts to demonstrate protection against gram-negative infection. Sakulramrung and Domingue, J. Inf. Dis., 151:995–1104 (1985); McCabe, et al., J. Infect. Dis., 1365:516 (1977); and Mullan, et al., Infect. Immun., 10:1195–1201 (1974). More recently, mouse and human monoclonal antibodies reactive with the conserved regions have been produced. Although these antibodies have sometimes shown partial in vivo efficacy in tailored model systems (Teng, et al., Proc. Natl. Acad. Sci. U.S.A. 82:1790 (1985); and Bogard and Kung, Patent Application No. WO85/01659), other laboratories have not been able to demonstrate similar effects. See Elkins and Metcalf, Infect. Immun. 48:597 (1985); and Gigliotti and Shenap, J. Inf. Dis. 151:1005–1011 (1985). Moreover, these antibodies generally do not react with (bind to) intact, viable gram-negative bacteria or to purified LPS molecules. These findings suggest that it is doubtful the core or lipid A portions of LPS on bacteria in their natural and infectious state would be accessible to antibody. It is also well accepted that anti-core or anti-lipid A antibodies will not react with gram-positive bacteria because the latter do not possess LPS. In view of these findings, it is unlikely that monoclonal antibodies to the conserved core or lipid A regions of LPS will be efficacious in the treatment of human gram-negative or, for that matter, gram-positive bacterial disease.

Thus, there still exists a significant need for human monoclonal antibodies that are broadly (intergenus) cross-protective against gram-positive and gram-negative bacterial diseases, as well as for methods for practical production and use of such antibodies. The present invention fulfills these needs.

SUMMARY OF THE INVENTION

Novel cell lines are provided which produce human monoclonal antibodies capable of specifically cross-reacting with a plurality of bacterial species by binding an accessible epitope comprising a non-core carbohydrate moiety present on at least two different bacterial species. Additionally, methods are provided for prophylactically treating a human patient susceptible to bacterial infection and therapeutically treating a patient suffering from such an infection by administering an effective amount of a composition comprising a plurality of human monoclonal antibodies, wherein at least one of these antibodies is capable of reacting with a non-core carbohydrate antigenic determinant shared by two or more bacterial species. The composition preferably includes a physiologically acceptable carrier, and may also contain any one or more of the following: additional human monoclonal antibodies capable of reacting with other bacterial genera; a gammaglobulin fraction from human blood plasma; a gammaglobulin fraction from human blood plasma, where the plasma is obtained from a human exhibiting elevated levels of immunoglobulins reactive with one or more bacterial genera; and one or more antimicrobial agents.

DESCRIPTION OF THE SPECIFIC EMBODIMENTS

In accordance with the present invention, novel cells capable of producing human monoclonal antibodies and compositions comprising such antibodies are provided, such compositions being capable of selectively reacting with a plurality of bacterial genera responsible for nosocomial, neonatal, or other infections, where individual antibodies typically react with non-core carbohydrate epitopes present on multiple bacterial genera. The subject cells have identifiable chromosomes in which the germ-line DNA from them or a precursor cell has rearranged to encode an antibody or binding fragment thereof having a binding site for an antigenic determinant (epitope) shared by carbohydrate molecules found on at least some serotypes of two or more bacterial genera. These human monoclonal antibodies can be used in a wide variety of ways, including for diagnosis, prophylaxis and therapy of bacterial disease.

Typically, the cells of the present invention will be cells capable of stable production of a human antibody in culture, particularly immortalized human lymphocytes that produce protective human monoclonal antibodies to non-core carbohydrate determinants on accessible molecules shared by at least two bacterial species. By "accessible" is meant that the non-core carbohydrate determinants are physically available in the environment of use for direct interaction with the monoclonal antibodies. The monoclonal antibodies so provided are useful in the treatment or prophylaxis of serious disease caused by a wide range of bacterial infections. Furthermore, those non-core carbohydrate molecules that are released into the surrounding environment are also free to interact directly with the antibody molecules and be cleared via the reticuloendothelial system.

The compositions containing the monoclonal antibodies of the present invention will typically be useful in the therapeutic and prophylactic treatment of nosocomial, neonatal, and other infections. As nosocomial infections are typically caused by infections from the following bacteria: *Escherichia coli, Pseudomonas aeruginosa, Klebsiella pneumoniae, Enterobacter aerogenes/cloacae, Serratia marcescens*, and *Streptococcus agalactiae* Group B, antibody compositions protective against two, three, four, or more of such bacteria would be preferred. Similarly, for neonatal use, such as in neonatal sepsis and meningitis, the antibodies are desirably specific for two or more of the following bacterial organisms: *Escherichia coli* K1, *Neisseria meningitidis* Group B, *Streptococcus agalactiae* Group B, and *Hemophilus influenzae* type B. Other common infectious bacteria include: *Staphylococcus aureus, Staphylococcus epidermidis, Streptococcus pneumoniae, Proteus mirabilis, Proteus vulgaris, Bacteroides fragilis, Pseudomonas cepacia, Mycobacterium tuberculosis, Providencia morganii, Salmonella typhi, Pneumocystis carinii, Acinetobacter herellea, Pasturella multocida, Klebsiella oxytoca*. For additional relevant pathogenic bacteria known to those skilled in the art, see, Hughs, J. M., et al., "Nosocomial Infection Surveillance, 1980–1982,"*Morb. Mort. Weekly Report*, 32:1SS–16SS (1983), and, generally, *Microbiology*, 3rd Edition, Davis, B. D., Dulbecco, R., Eisen, H. N., Ginserberg, H. S., Wood, W. B., and McCarty, M., Eds., Harper and Row (1980), both of which are incorporated herein by reference. The monoclonal antibodies will react with individual members or all of the members of a particular bacterial species, where the members may be distinguished by their surface epitopes, particularly LPS or capsule sites, e.g. serotypes.

The unexpected discovery of monoclonal antibody cross-reactivity across various bacterial species, including the clinically important species listed above, provides novel means for therapeutic and prophylactic treatments. By utilizing pre-selected cross-reactive antibodies in combination, a mixture of a few antibodies can be produced for treatment against a number of different species of infectious bacteria.

By way of example, and not of limitation, a mixture of two monoclonal antibodies, one cross-reactive with at least two bacterial species of clinical significance and the second cross-reactive with at least two or three different species, will be useful in treatment against four, five, six or more different species. Adding a third or fourth monoclonal antibody, each one of which is cross-reactive with at least two clinically important species—even if one or more of the species is the same as that recognized by the first and/or second antibody, will increase usefulness in treatment against five to ten or more species. Of course, it may be necessary to also add one or more monoclonal antibodies, each specific for just a single pre-selected bacterial species, for example, when monoclonal antibodies cross-reactive with that species are unavailable.

Similarly, new methods of treating bacterial infections are also provided based on the discovery. Again, by way of example and not limitation, one novel method entails treating a patient suspected of having or being susceptible to a bacterial infection caused by a selected bacterial species. The treatment includes administering a composition comprising a monoclonal antibody reactive with the bacterial species suspected of causing the infection, wherein the monoclonal antibody was initially characterized as reactive with a different bacterial species.

Another example is a method of treating bacterial infections by administering compositions comprising a plurality of monoclonal antibodies reactive with a substantial proportion (i.e., greater than 50%, preferably 60% to 80% or more, most preferably about 90%) of pre-selected, clinically important bacterial species, wherein the number of antibodies is at least about two less than the number of bacterial species. Typically, if "n" represents the number of bacterial species, the composition will comprise about n–2 antibodies, more typically about n–4 to n–8 or less antibodies for treatment against up to about 15 to 20 bacterial species. In situations where treatment against a broad spectrum (e.g., 25 to 50 or more) of bacterial species is desired, the composition will typically comprise n–10 to n–20 antibodies or less.

Preparation of monoclonal antibodies can be accomplished by immortalizing the expression of nucleic acid sequences that encode for antibodies or binding fragments thereof specific for a non-core carbohydrate epitope present on multiple bacterial species. Typically, the monoclonal antibodies are produced by cell-driven Epstein-Barr Virus (EBV) transformation of lymphocytes obtained from human donors who are, or have been exposed to the respective gram-negative bacteria. The antibody-secreting cell lines so produced are characterized as continuously growing lymphoblastoid cells that possess a diploid karyotype, are Epstein-Barr nuclear antigen (EBNA) positive, and secrete monoclonal antibody of either IgG, IgM, IgA, or IgD isotype. The cell-driven transformation process itself is an invention assigned to Genetic Systems Corporation and is described in detail in U.S. Pat. No. 4,464,465 which is incorporated herein by reference. The monoclonal antibodies may be used intact, or as fragments, such as $F_v$, Fab, $F(ab')_2$, but usually intact.

Alternatively, cell lines producing the antibodies could be produced by cell fusion between suitably drug-marked human myeloma, mouse myeloma, or human lymphoblastoid cells with human B-lymphocytes to yield hybrid cell lines.

The cell lines of the present invention may find use other than for the direct production of the human monoclonal antibodies. The cell lines may be fused with other cells (such as suitably drug-marked human myeloma, mouse myeloma, or human lymphoblastoid cells), to produce hybridomas, and thus provide for the transfer of the genes encoding the human monoclonal antibodies. Alternatively, the cell lines may be used as a source of the DNA encoding the immunoglobulins, which may be isolated and transferred to cells by techniques other than fusion. In addition, the genes encoding the monoclonal antibodies may be isolated and used in accordance with recombinant DNA techniques for the production of the specific immunoglobulin in a variety of hosts. Particularly, by preparing cDNA libraries from messenger RNA, a single cDNA clone, coding for the immunoglobulin and free of introns, may be isolated and placed into suitable prokaryotic or eukaryotic expression vectors and subsequently transformed into a host for ultimate bulk production.

The lymphoblastoid or hybrid cell lines may be cloned and screened in accordance with conventional techniques, with the antibodies that are capable of binding to the epitopes of different bacterial genera detected in the cell supernatants.

The monoclonal antibodies of this invention find particular utility as components of pharmaceutical compositions containing a therapeutic or prophylactic amount of at least one of the monoclonal antibodies of this invention in conjunction with a pharmaceutically effective carrier. A pharmaceutical carrier can be any compatible, non-toxic substance suitable for delivery of the monoclonal antibodies to the patient. Sterile water, alcohol, fats, waxes, and inert solids may be included in the carrier. Pharmaceutically accepted adjuvants (buffering agents, dispersing agents) may also be incorporated into the pharmaceutical composition. Such compositions can contain a single monoclonal antibody cross-reactive with non-core carbohydrate epitopes shared by two or more bacterial species that cause, for example, nosocomial and neonatal (e.g., sepsis or meningitis) infections. Alternatively, a pharmaceutical composition can contain two or more monoclonal antibodies to form a "cocktail." For example, a cocktail containing human monoclonal antibodies each protective against two or more gram-negative bacterial genera responsible for human infections, would have activity against the great majority of the common clinical isolates. If desired, one or more of the monoclonal antibodies could be selected to be cross-reactive with gram-positive bacteria as well, making even broader product applications feasible.

Of interest are prophylactic and/or therapeutic monoclonal antibody compositions capable of reacting with non-core carbohydrate determinants shared by three or more, usually at least five, and more usually at least ten, and up to fifteen or more bacterial serotypes, which includes at least two, usually at least three, more usually at least five, and usually fewer than ten bacterial genera.

Of particular interest are monoclonal antibody compositions which react with at least about three, preferably at least about five and up to and including all of the following common nosocomial infection-causing bacteria: *Escherichia coli*, *Pseudomonas aeruginosa*, *Klebsiella pneumoniae*, *Enterobacter aerugenes/cloacae*, *Serratia marcescens*, and *Streptococcus agalactiae* Group B. For treatment of neonatal infections, desirably the compositions will react with at least two, usually at least three, and more usually at least four and up to and including all of the following infection-causing bacterial genera: *Escherichia coli* K1, *Neisseria meningitidis* Group B, *Streptococcus agalactiae* Group B, *Hemophilus influenzae* type B, *Staphylococcus aureus*, and *Staphylococcus epidermidis*.

Each of the compositions will include at least two, usually at least three to five, and more usually six to ten human monoclonal antibodies, where at least one antibody reacts with non-core carbohydrate epitopes (e.g., of the LPS molecules) shared by two or more bacterial genera and providing protection. Typically, the antibody will not bind to all serotypes of each bacterium, but may bind to two, three or more serotypes. Desirably, there will be at least one monoclonal antibody which binds to an accessible non-core carbohydrate moiety of at least two genera of gram-negative bacteria and at least one monoclonal antibody that binds to an accessible carbohydrate moiety of a gram-negative bacterium and a gram-positive bacterium.

The mole ratio of the various monoclonal antibody components will usually not differ one from the other by more than a factor of 10, more usually by not more than a factor of 5, and will usually be in a mole ratio of about 1:1–2 to each of the other antibody components.

The human monoclonal antibodies may also find use individually, particularly where the pathogen has been identified or is limited to a narrow range of pathogens within the binding spectrum of the particular antibody.

The human monoclonal antibodies of the present invention may also be used in combination with other monoclonal antibodies as described in detail on U.S. Pat. No. 5,378,812 as well as existing blood plasma products, such as commercially available gamma globulin and immune globulin products used in prophylactic or therapeutic treatment of bacterial disease in humans. Preferably, for immune globulins the plasma will be obtained from human donors exhibiting elevated levels of immunoglobulins reactive with various infectious bacterial genera. See generally, the compendium "Intravenous Immune Globulin and the Compromised Host," *Amer. J. Med.*, 76(3a), Mar. 30, 1984, pgs 1–231, which is incorporated herein by reference.

The monoclonal antibodies of the present invention can be used as separately administered compositions given in conjunction with antibiotics or antimicrobial agents. Typically, the antimicrobial agents may include a penicillin or cephalosporin (e.g., carbenicillin, penicillin G, or the like) in conjunction with an aminoglycoside (e.g., gentamicin, tobramycin, etc.), but numerous additional agents (e.g., cephalosporins, sulfa drugs, etc.) well-known to those skilled in the art may also be utilized.

The human monoclonal antibodies and pharmaceutical compositions thereof of this invention are particularly useful for oral or parenteral administration. Preferably, the pharmaceutical compositions may be administered parenterally, i.e., subcutaneously, intramuscularly or intravenously. Thus, this invention provides compositions for parenteral administration which comprise a solution of the human monoclonal antibody or a cocktail thereof dissolved in an acceptable carrier, preferably an aqueous carrier. A variety of aqueous carriers can be used, e.g., water, buffered water, 0.4% saline, 0.3% glycine and the like. These solutions are sterile and generally free of particulate matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example sodium acetate, sodium chloride, potassium chloride, calcium chloride, sodium lactate, etc. The concentration of antibody in these formulations can vary widely, i.e., from less than about 0.5%, usually at or at least about 1% to as much as 15 or 20% by weight and will be selected primarily based on fluid volumes, viscosities, etc., in accordance with the particular mode of administration selected.

Thus, a typical pharmaceutical composition for intramuscular injection could be made up to contain 1 ml sterile buffered water, and 50 mg of monoclonal antibody. A typical composition for intravenous infusion could be made up to contain 250 ml of sterile Ringer's solution, and 150 mg of monoclonal antibody. Actual methods for preparing parenterally administrable compositions will be known or apparent to those skilled in the art and are described in more detail in, for example, *Remington's Pharmaceutical Science*, 15th Ed., Mack Publishing Company, Easton, Pa. (1980), which is incorporated herein by reference.

The monoclonal antibodies of this invention can be lyophilized for storage and reconstituted in a suitable carrier prior to use. This technique has been shown to be effective with conventional immune globulins and art-known lyophilization and reconstitution techniques can be employed. It will be appreciated by those skilled in the art that lyophilization and reconstitution can lead to varying degrees of antibody activity loss (e.g., with conventional immune globulins, IgM antibodies tend to have greater activity loss than IgG antibodies) and that use levels may have to be adjusted to compensate.

The compositions containing the present human monoclonal antibodies or a cocktail thereof can be administered for the prophylactic and/or therapeutic treatment of bacterial infections. In therapeutic application, compositions are administered to a patient already infected, in an amount sufficient to cure or at least partially arrest the infection and its complications. An amount adequate to accomplish this is defined as a "therapeutically effective dose." Amounts effective for this use will depend upon the severity of the infection and the general state of the patient's own immune system, but generally range from about 1 to about 200 mg of antibody per kilogram of body weight with dosages of from 5 to 25 mg per kilogram being more commonly used. It must be kept in mind that the materials of this invention may generally be employed in serious disease states, that is life-threatening or potentially life-threatening situations, especially bacteremia and endotoxemia. In such cases, in view of the absence of extraneous substances and the absence of "foreign substance" rejections which are achieved by the present human monoclonal antibodies of this invention, it is possible and may be felt desirable by the treating physician to administer substantial excesses of these antibodies.

In prophylactic applications, compositions containing the present antibody or a cocktail thereof are administered to a patient not already infected by the corresponding bacteria to enhance the patient's resistance to such potential infection. Such an amount is defined to be a "prophylactically effective dose." In this use, the precise amounts again depend upon the patient's state of health and general level of immunity, but generally range from 0.1 to 25 mg per kilogram, especially 0.5 to 2.5 mg per kilogram.

Single or multiple administrations of the compositions can be carried out with dose levels and pattern being selected by the treating physician. In any event, the pharmaceutical formulations should provide a quantity of the antibody(ies) of this invention sufficient to effectively treat the patient.

Monoclonal antibodies of the present invention can further find a wide variety of utilities in vitro. By way of example, the monoclonal antibodies can be utilized for bacterial typing, for isolating specific bacterial strains or fragments thereof, for vaccine preparation, or the like.

For diagnostic purposes, the monoclonal antibodies may either be labeled or unlabeled. Typically, diagnostic assays entail detecting the formation of a complex through the binding of the monoclonal antibody to the LPS of the organism. When unlabeled, the antibodies find use in agglutination assays. In addition, unlabeled antibodies can be used in combination with other labeled antibodies (second antibodies) that are reactive with the monoclonal antibody, such as antibodies specific for human immunoglobulin. Alternatively, the monoclonal antibodies can be directly labeled. A wide variety of labels may be employed, such as radionuclides, fluorescers, enzymes, enzyme substrates, enzyme cofactors, enzyme inhibitors, ligands (particularly haptens), etc. Numerous types of immunoassays are available, and by way of example, some of the assays are described in U.S. Pat. Nos. 3,817,827; 3,850,752; 3,901,654; 3,935,074; 3,984,533; 3,996,345; 4,034,074; and 4,098,876, all of which are incorporated herein by reference.

Commonly, the monoclonal antibodies of the present invention are utilized in enzyme immunoassays, where the subject antibodies, or second antibodies from a different species, are conjugated to an enzyme. When a sample, such as human blood or lysate thereof, containing one or more bacteria of a certain genus or serotype, is combined with the subject antibodies, binding occurs between the antibodies and those molecules exhibiting the selected epitopes. Such cells may then be separated from the unbound reagents, and a second antibody (labeled with an enzyme) added. Thereafter, the presence of the antibody-enzyme conjugate specifically bound to the cells is determined. Other conventional techniques well known to those skilled in the art may also be utilized.

Kits can also be supplied for use with the subject antibodies in the detection of bacterial infection or for the presence of a selected antigen. Thus, the subject monoclonal antibody composition of the present invention may be provided, usually in a lyophilized form in a container, either alone or in conjunction with additional antibodies specific for other gram-negative bacteria. The antibodies, which may be conjugated to a label or unconjugated, are included in the kits with buffers, such as Tris, phosphate, carbonate, etc., stabilizers, biocides, inert proteins, e.g., bovine serum albumin, or the like. Generally, these materials will be present in less than about 5% wt. based on the amount of active antibody, and usually present in total amount of at least about 0.001% wt. based again on the antibody concentration. Frequently, it will be desirable to include an inert extender or excipient to dilute the active ingredients, where the excipient may be present in from about 1 to 99% wt. of the total composition. Where a second antibody capable of binding to the monoclonal antibody is employed, this will usually be present in a separate vial. The second antibody is typically conjugated to a label and formulated in an analogous manner with the antibody formulations described above.

The following experimental data and information are offered by way of example and not limitation.

EXAMPLE I

This EXAMPLE demonstrates methods for the production of a human monoclonal antibody that possesses intergenus cross-reactivity against members of the genera *Escherichia coli* (*E. coli*), *Serratia marcescens* (*S. marcescens*), *Klebsiella pneumoniae* (*K. pneumoniae*), and *Enterobacter aerogenes* (*E. aerogenes*). Further, this EXAMPLE demonstrates the in vivo protective activity of said antibody, against a lethal challenge of homologous (cross-reacting) *E. coli*, and *E. aerogenes* serotypes.

A. Obtaining Suitable Human Cells

Suitable human B cells (lymphocytes) were obtained from the peripheral blood of an individual known to have harbored the disease cystic fibrosis. Mononuclear cells were separated from the peripheral blood by standard centrifugation techniques on Ficoll-Paque (Boyum, A., "Isolation of Mononuclear Cells and Granulocytes From Human Blood," Scand. J. Clin. Lab. Invest., 21. Suppl. 97:77–89, (1968)) and washed twice in calcium-magnesium free phosphate buffered saline (PBS) prior to suspension in 1 ml of 90% fetal bovine serum (FBS) and 10% dimethyl sulfoxide and freezing at $-196°$ C. in liquid nitrogen.

When the mononuclear cells were to be transformed, an ampule containing $5 \times 10^7$ cells was rapidly thawed at 37° C. The cell suspension was added to 10 ml of Iscove's medium containing 15% FBS and centrifuged at room temperature for 10 min at 250×g. The mononuclear cells were depleted of T cells (lymphocytes) using a modified E-rosetting procedure. Briefly, the cells were resuspended to a concentration of $1 \times 10^7$ cells/ml in PBS containing 20% FBS at 4° C. One ml of this suspension was placed in a 17×100 mm polystyrene round bottom tube to which was added $1 \times 10^9$ 2-amino-ethyl-isothiouronium bromide (AET)-treated sheep red blood cells from a 10% (v/v) solution in Iscove's medium (Madsen, M. and Johnson, H. E., "A Methodological Study of E-rosette Formation Using AET Treated Sheep Red Blood Cells," J. Immun. Methods, 27:61–74, (1979)). The suspension was vigorously mixed for 5–10 min at 4° C. and the E-rosetted cells were removed by centrifugation through Ficoll-Paque for 8 min at 2500×g at 4° C. E-rosette negative peripheral blood mononuclear cells (E⁻PMBC) banding at the interface were washed once in Iscove's medium and resuspended in same containing 15% w/v FBS (g/ml), L-glutamine (2 mM/1), sodium pyruvate (1 mM/1), penicillin 100 IU/ml), streptomycin (100 µg/ml), hypoxanthine ($1 \times 10^{-4}$M), aminopterin ($4 \times 10^{-7}$M) and thymidine ($1.6 \times 10^{-7}$M). This medium is hereafter referred to as HAT medium.

B. Cell-Driven Transformation of Peripheral Blood Mononuclear Cells

Cell-driven transformation of the E⁻PBMC was accomplished by cocultivating the E⁻PBMC with a transforming cell line. The transforming cell line was an EBNA positive human lymphoblastoid cell line derived by ethylmethane sulphonate mutagenesis of the GM 1500 lymphoblastoid cell line. Selection in the presence of 30 µg/ml 6-thioguanine rendered the cells hypoxanthineguanine phosphoribosyl transferase deficient and thus HAT sensitive. The cell line is denominated the 1A2 cell line and was deposited at the American Type Culture Collection (A.T.C.C.) on Mar. 29, 1982 under A.T.C.C. No. CRL 8119. 1A2 cells in logarithmic growth phase were suspended in HAT medium and combined with the E⁻PBMC at a ratio of 30 1A2 cell per E⁻PBMC. The cell mixture was plated into 10 round-bottom 96-well microtiter plates at a concentration of 62,000 cells/well in a volume of 200 µl/well, and the culture incubated at 37° C. in a humidified atmosphere containing 6% $CO_2$. Cultures were fed five days post transformation by replacement of half the supernatant with fresh HAT medium. The wells were observed every other day on an inverted microscope for signs of cell proliferation. Ten days after plating the cell mixture and after the 1A2 cells had died due to HAT selection, feeding of the the wells was accomplished with a new media formulation identical to HAT media except that it lacked the aminopterin component. Fifteen days post plating, it was observed that 100% of the wells contained proliferating cells and that in most of the wells, the cells were of sufficient density for removal and testing of supernatants for anti-*E. coli* or anti-*S. marcescens* antibody.

C. Detection of Specific Antibody Secreting Cells

Supernatants were screened for the presence of anti-*E. coli* or anti-*S. marcescens* antibodies using an enzyme-linked immunosorbent assay (ELISA) technique (Engvall, E., "Quantitative Enzyme Immunoassay (ELISA) in Microbiology," Med. Biol., 55:193–200, (1977)). The antigen plates consisted of a series of flat-bottom 96-well Immunlon 2 microtiter plates, the wells of which contained a mixture of either viable *E. coli* or *S. marcescens* serotypes affixed to the well surfaces with poly-L-lysine (PLL). Briefly, 50 µl of PLL (1 µg/ml) in PBS was added to each well for 30 min at room temperature (RT). The plates were washed three times with PBS and either PBS or 50 µl of a mixed bacteria suspension at O.D.$_{660}$=0.2 was added to each well. The plates were incubated at 37° C. for 60 min and washed 3 times with saline/0.02% Tween 20 (saline/T) to removed unattached bacteria. Various antigen plates used in the screen included: 1) a mixture of *E. coli* serotypes 01 (A.T.C.C. No. 23499) and 04 (A.T.C.C. No. 12791); 2) a mixture of *S. marcescens* serotypes 07, 015, 016 and 018 (all reference typing strains were obtained from the Communicable Disease Center (CDC) Atlanta, Ga.); and 3) a microtiter plate with no bacteria.

For the ELISA procedure, assay wells were first blocked with 200 µl of a mixture containing 5% w/v dry non-fat milk, 0.0001% Anti-Foam A, and 0.01% w/v Thimerosal in 500 ml PBS to prevent non-specific protein binding. After incubation for 1 hour at RT, the plates were washed three times with 200 µl/well/wash of saline/T. To each well was added 50 µl of a mixture containing 0.1% Tween 20 and 0.2% bovine serum albumin in PBS (PTB). Supernatants from wells of the culture plate were replica plated into corresponding wells of the antigen and control plates (50 µl/well) and the plates were incubated at RT for 30 min. The supernatants were then removed, plates were washed five times with saline/T, and 50 µl of biotinylated goat anti-human immunoglobulin (Ig)(TAGO #9303040 diluted 1:250 in PTB) was added to each well. After a 30 min incubation at RT the biotinylated reagent was removed, the wells washed five times with saline/T and 50 µl of a preformed avidin:biotinylated horseradish peroxidase complex (Vectastain ABC Kit, Vector Laboratories) was added to each well. After 30 min. at RT the Vectastain ABC reagent was removed, the wells were washed five times with saline/T, and 100 µl of substrate (0.8 mg/ml ortho-phenylenediamine dihydrochloride in 100 mM citrate buffer, pH 5.0 plus 0.03% $H_2O_2$ in deionized $H_2O$ mixed in equal volumes just before plating) added to each well. After 30 min incubation in the dark, 50 µl of 3N $H_2SO_4$ was added to each well to terminate the reaction. Culture supernatants which contained antibody reactive with the bacteria coated plates were detected by measuring absorbance at 490 nm on a Dynatech MR 580 microELISA reader.

Culture supernatants from six transformations were analyzed by the above method resulting in the identification of one well (7D7) which possessed activity on the *E. coli* and *S. marcescens* serotype plates, but not on the control plates. It was determined in subsequent ELISA's with individual *E. coli* serotypes, that this well contained antibody reactive with at least, the *E. coli* serotypes: 08, (A.T.C.C. No. 23504), and 075 (A.T.C.C. No. 12798), but not 04, 06:K2, 08:K8, 09:K9 or 022:K13 (A.T.C.C. Nos. 12791, 19138, 23501, 23505 and 23517, respectively). Further, this well contained antibody reactive with the *S. marcescens* serotypes 012, 013 and 015, but not any other of the twenty known *S. marcescens* LPS serotypes.

D. Cloning of Specific Antibody Producing Cells

The cells in well 7D7 were subjected to several rounds of cloning (four) until all clonal supernatants assayed by the above ELISA procedure gave a positive reaction on *E. coli* serotypes 08 and 075 and on *S. marcescens* serotypes 012, 013 and 015. There was never an example when any clonal supernatant demonstrated segregation in its reactivity pattern, suggesting that the culture supernatant from well 7D7 possessed true intergenus cross-reactivity to the *E. coli* and *S. marcescens* serotypes set forth and did not contain more than one cell line (each demonstrating individual serotype reactivity). Cells were cloned by limiting dilution in round-bottom 96-well plates in the absence of feeder cells. Media consisted of Iscove's medium containing 15% v/v FBS, L-glutamine (2 mM/l), sodium pyruvate (1 mM/l), penicillin (100 IU/ml), and streptomycin (100 µg/ml). Cultures were fed every three days by replacement of half the supernatant with fresh media. In general, wells were of sufficient lymphoblastoid cell density between 2 and 3 weeks post-plating for analysis of anti-*E. coli* and *S. marcescens* serotype specificity.

Thus, in this experiment one cloned transformed human cell line was achieved which is continuous (immortal) and secretes a human monoclonal antibody to a determinant on the surface of the *E. coli* and *S. marcescens* serotypes set forth.

Prior to filing of this patent application, the continuous transformed human cell line identified as 7D7 was deposited with the American Type Culture Collection, Rockville, Md. as A.T.C.C. No. CRL 9009.

E. Further Characterization of Intergenus Cross-Reactivity

Antibody from the cloned 7D7 cell line was assayed for further intergenus cross-reactivity by a modification of the standard immunoblotting technique. Specifically, cross-reactivity to the bacteria *K. pneumoniae*, *E. aerogenes*, and *E. cloacae* was investigated by spotting bacteria onto a gridded nitrocellulose paper disc, reacting the disc containing the bacteria with said antibody, and developing the antibody reactions with an alkaline pnosphatase/nitroblue tetrazolium enzyme system. Briefly, 1.0 µl of bacteria (O.E.$_{660}$=0.4) was spotted per grid section of a nitrocellulose paper disc (Schleicher and Schuell, 37 mm nitrocellulose disc, gridded, 0.45 µm). Each disc can conveniently hold 60 different bacterial samples. The spotted discs were air-dried, fixed in 25% v/v isopropanol for 30 min. and blocked for 10 min in the non-fat dry milk reagent as described for the ELISA method. The blocked discs were washed three times for 5 min each in PBS/Tween 20 and were transferred to the lids of 35×10 mm tissue culture dishes. The antibody containing supernatant (1.0 ml) was added to the lid and was incubated at RT for 60 min. Following three 5 min washes in PBS/Tween 20, 1–2 ml of 1:1000 diluted (PBS) alkaline phosphatase conjugated goat-anti-human immunoglobulin (TAGO, Burlingame, Calif.) was added for 60 min at RT. The discs were washed as above, and were submerged in 1–2 ml of fresh substrate prepared as follows: 16.5 mg of bromo-chlorindolylphosphate and 8.5 mg nitroblue tetrazolium were dissolved in 50 ml of alkaline phosphatase buffer (0.1M Tris-HCl, pH 9.5 with 0.1M NaCl and 5 mM $MgCl_2$), the solution was kept in the dark, and filtered immediately before using. After appropriate color development (10–15 min), the reaction was quenched by rinsing the disc in several changes of distilled water. The developed discs can be stored after drying.

The discs contained; 50 *K. pneumoniae* capsule-typed reference strains obtained from Dr. George Kenney, University of Washington, Department of Pathobiology, Seattle, Wash. and the American Type Culture Collection, 4 *E. aerogenes* clinical blood isolates, and 6 *E. cloacae* clinical blood isolates (blood isolates obtained from Harborview Hospital, Seattle, Wash.). The Enterobacter isolates were typed (speciated) using the API 20E System of 23 standardized biochemical tests (API Analytab Products, Plainview, N.Y.). This method identities the genus and species of gram-negative bacteria, but not the serotype. Therefore, the Enterobacter, unlike the *E. coli*, *S. marcescens*, and *K. pneumoniae*, are not identified as to serotype, but only as to genus and specie.

From these experiments, the 7D7 antibody was observed to possess further intergenus cross-reactivity. This antibody reacted with the following serotypes:

| K. pneumoniae | E. coli | S. marcescens | E. aerogenes |
|---|---|---|---|
| K14,57,60 | 08,75 | 012,13,15 | Clinical Isolates |

Thus, the human monoclonal antibody 7D7 was observed to possess intergenus cross-reactivity to bacteria belonging to the species *E. coli*, *S. marcescens*, *K. pneumoniae*, *E. aerogenes* but not *E. cloacae*.

F. Characterization of Monoclonal Antibodies

The finding that the Monoclonal Antibody cross-reacted with several different bacterial genera suggested the antibody was directed against a shared protein or carbohydrate. These two molecular species have been shown to account for intragenus cross-reactions (Mutharia, L. and Hancock, R. E. W., "Characterization of Two Surface-Localized Antigenic Sites on Porin Protein F of *Pseudomonas aeruginosa*," Canadian J. of Microbiol., 31:381–386, (1985) and Orskov, F. and Orskov, I., "Serotyping of *Escherichia Coli,* " in *Methods in Microbiology,* Vol. 14, Bergan, T., ed. Academic Press, Orlando, Fla., 43–112 (1984)).

Biochemical characterization of the molecular species recognized by the 7D7 antibody was accomplished by immunoblot analysis. Briefly, washed bacteria from a 20 ml overnight broth culture (for *E. coli, S. marcescens,* and *E. aerogenes* serotypes) or from overnight grown plates (*K. pneumoniae*) were extracted in 1.0 ml of a solution containing 64 ml of 50 mM Tris pH 7.6, 30 ml of glycerol, 0.3 gm of deoxycholate (sodium salt), 0.14 ml beta-mercaptoethanol, and 6 ml deionized water (Schechter, I. and Block, K., "Solubilization and Purification of trans-Formesyl Pyrophosphate-Squalene Synthetase, "J. Biol Chem., 246:7690–7696, (1971)). After 18 hour incubation at 4° C., the suspension was centrifuged at 10,000×g for 10 min. The supernatant was removed and the protein was quantitated using the Bio-Rad Protein Assay (Bio-Rad Laboratories, Richmond, Calif.). Between 100 and 1000 ng of protein (varies for each bacterial extract) from each bacteria were each subjected to sodium dodecyl sulphate (SDS)—polyacrylamide gel electrophoresis (Kusecek, B., et al., "Lipopolysaccharide, Capsule, and fimbriae as Virulence Factors Among 01, 07, 016, 018 or 075 and K1, K5 or K100 *Escherichia coli*," Infection and Immunity, 43:368–379 (1984)). Separated molecular species were transferred from the gel to a nitrocellulose membrane (NCM) as described elsewhere (Towbin, H., et al., "Electrophoretic Transfer of Proteins From Polyacrylamide Gels to Nitrocellulose Sheets: Procedure and Some Applications," Proc. Natl. Acad. Sci., 76:4350–4354, (1979)) and the NCM blot blocked for 1 hour in PBS-Tween (Batteiger, B, et al., "The Use of Tween 20 as a Blocking Agent in the Immunological Detection of Proteins transferred to Nitrocellulose Membranes," J. Immunol. Meth. 55:297–307, (1982)). The blot was incubated for 1 hour at RT in 10 ml of spent culture supernatant from the 7D7 line. Following four 5 min rinses in PBS-Tween, the blot was incubated in goat anti-human Ig conjugated to alkaline phosphatase and developed as described herein for the bacteria-nitrocellulose disc assay. Positive reactions were noted in all tracks that contained deoxycholate extracts of the bacteria described herein. In these tracks the 7D7 antibody appeared to recognize a series of regularly spaced molecular entities giving rise to a ladder-like pattern on the immunoblot. This profile was entirely consistent with that seen in polyacrylamide gel electrophoretic analysis of LPS in the presence of SDS, where it has been demonstrated that the heterogeneous size profile exhibited by the bands is due to a population of LPS molecules differing by weight increments equivalent to the number of O-antigenic oligosaccharide side chain units present per molecule (Pavla, E. T. and Makela, P. H., "Lipopolysaccharide Heterogeneity in *Salmonella typhimurium* Analyzed by Sodium Dodecyl Sulfate/Polyacrylamide Gel Electrophoresis," Eur. J. Biochem., 107:137–143, (1980) and Goldman, R. C. and Leive, L., "Heterogeneity of Antigenic-Side-Chain Length in Lipopolysaccharide from *Escherichia coli* 0111 and *Salmonella typhimurium* LT2, Eur. J. Biochem., 107:143–154, (1980)). These data indicate that the monoclonal antibody 707 is directed against an antigenic determinant shared by the LPS molecules found on some serotypes of *E. coli, S. marcescens, K. pneumoniae,* and *E. aerogenes.*

To further define the molecular nature of the antigen, the deoxycholate extracts were treated, prior to their electrophoresis, with the proteolytic enzyme Proteinase K (Eberling, W., et al., "Proteinase K from *Tritirachium album* Limber," Eur. J. Biochem. 47:91–97 (1974)). To prepare the sample, 10 µg of Proteinase K was added to 50 µg of sample protein and the mixture was heated to 65° C. for 60 min. The samples were electrophoresed and immunoblotted as described herein. The immunoblot patterns observed after Proteinase K treatment were identical to those patterns observed without treatment and thus suggest that the antigen reactive with the 7D7 antibody is not protein in nature.

To specifically address whether 7D7 reacted with a carbohydrate epitope, the electrotransferred deoxycholate sample was subjected to mild periodate oxidation prior to reacting the nitrocellulose paper with antibody. This reaction has been shown to destroy carbohydrate determinants, and thus their subsequent reactivity with antibody, without altering protein or lipid epitopes (Woodward, M. P., et al., "Detection of Monoclonal Antibodies Specific for Carbohydrate Epitopes Using Periodate Oxidation," J. of Immunol. Methods, 78:143–153, (1985)). Briefly, after the electro-blotted nitrocellulose paper containing the electrophoresed sample was blocked with PBS-Tween, as described herein, the paper was rinsed with 50 mM acetic acid sodium acetate pH 4.5 buffer. The nitrocellulose paper was incubated in 50 mM periodic acid dissolved in the acetic acid buffer for 60 min in the dark at RT. The treated paper was rinsed three times in PBS-Tween and reacted with the antibody as described herein. Electro-blotted deoxycholate extracts treated in this manner were no longer reactive with the 7D7 monoclonal antibody. These data strongly indicate that the epitope recognized by this antibody is a carbohydrate present on the LPS molecule of the bacteria described here.

The isotype of the 7D7 monoclonal antibody was determined in an ELISA procedure similar to the specificity tests described above except that biotinylated goat anti-human IgG (gamma-chain specific, TAGO) or biotinylated goat anti-human IgM (mu-chain specific, TAGO) was used as the second step reagent instead of the more broadly reactive biotinylated goat anti-human Ig. Both reagents were used at a 1:500 dilution and the antigen plate contained pools of PLL immobilized *E. coli* 08 and 075 strains. Positive reaction of the 7D7 monoclonal antibody with the *E. coli* strains was observed only with the anti-IgM reagent, demonstrating an IgM isotype for the monoclonal antibody. It will be appreciated by those skilled in the art that if the above process were repeated several times and the isotypes of intergenus cross-reactive monoclonal antibodies so obtained were determined, one would find additional e.g., IgM and IgG isotypes (Frosch, M., et al;, "NZB Mouse System For Production of Monoclonal Antibodies to Weak Bacterial Antigens: Isolation of an IgG Antibody to the Polysaccharide Capsules of *Escherichia coli* K1 and Group B Meningocci," Proc. Natl. Acad. Sci., 82:1194–1198, (1985)).

G. In Vitro Activity

In vitro functional activity of the 7D7 monoclonal antibody was examined in an in vitro opsonophagocytosis assay which compared the bacteriocidal activity of the antibody in the presence and absence of both human neutrophils and human complement.

Bacteria were prepared by either inoculating 10 ml of tryptic soy broth (TSB) with 50 µl of an overnight broth culture (for *E. coli, S. marcescens,* and *E. aerogenes*) or for *K. pneumoniae,* streaking a petri dish containing Worfel-Ferguson Agar. For broth cultures, the tubes were incubated at 37° C. on a shaker for 3 hours at which time 1.5 ml of the culture was centrifuged for 1 min at 10,000×g, the spent culture media discarded, and the pellet was suspended in 3.5 ml of Hank's balanced salt solution containing 0.1% gelatin and 5 mM HEPES (HBSS/Gel). For the agar plate grown bacteria, the colonies were scraped off the plate into sterile HBSS/Gel. The bacterial concentrations for bacteria grown under both conditions were adjusted to $3 \times 10^3$ bacteria/ml by measuring the O.D.$_{660}$ and making the appropriate dilutions (approximately 1:50,000). Human neutrophils were isolated according to van Furth and Van Zwet ("In Vitro Determination of Phagocytosis and Introcellular Killing by Polymorphonuclear and Mononuclear Phagocytes," in *Handbook of Experimental Immunology*, Vol. 2, D. M. Weir, ed., 2nd edition, Blackwell Scientific Publications, Oxford, 36.1–36.24 (1973)) with several modifications. Buffy coat from 10 ml of heparinized blood was underlayed with Ficoll-Pacque and centrifuged. The red blood cell (RBC) pellet was washed once with RPMI 1640 medium and resuspended in an equal volume of 37° C. PBS. Three ml of this suspension was added to 6 ml of 2% dextran (in 37° C. PBS) and the contents gently but thoroughly mixed end over end. After a 20 min incubation at 37° C. to allow the RBC's to sediment, the supernatant (containing neutrophils) was removed, washed twice in 4° C. PBS, once in HBSS/Gel, and suspended in same to $5 \times 10^7$ neutropnils/ml. For the complement source used with *E. coli* and *S. marcescens*, human serum was twice adsorbed with live bacteria pools (Bjornson, A. B. and Michael, J. G., "Factors in Human Serum Promoting Phagocytosis of *Pseudomonas aeruginosa* I. Interaction of Opsonins with the Bacterium," J. of Inf. Dis., 130Suppl:S119-S126 (1974)) corresponding to the organisms used in the assay. This serum was further adsorbed with boiled Zymosan (Bjornson, supra) to remove the serum component properidin, a molecule necessary for the activation of the alternate complement pathway. For opsonophagocytic assays using *K. pneumoniae* and *E. aerogenes*, the complement source was unadsorbed normal human serum used at 1% final concentration.

Plates used to quantify the number of surviving/destroyed bacteria were prepared beginning with warming of 24 well plates at 37° C. for 3–5 hours. A 0.4% solution of agarose in TSB was prepared by autoclaving the mixture for 5 min and allowing it to cool to 50° C. in a water bath. Approximately 15 min before the end of the final incubation period in the opsonophagocytosis assay, a 24 well plate was removed from the 37° C. incubator, placed on a 42° C. hot plate and 0.4 ml of TSB/agarose was added to each well. The plate was immediately returned to the 37° C. incubator such that the agarose never cooled below 37° C.

For the assay, 25 µl of 7D7 culture supernatant and 25 µl of an appropriate bacterial strain were added in duplicate to 96 well round bottom microtiter plates and incubated at RT for 30 min. This was followed by the addition of 15 µl of human complement, 15 µl of human neutrophils ($5 \times 10^6$/ml), and 70 µl HBSS/Gel. The entire surface of the plate was wiped with a sterile cotton swab, an adhesive plastic plate sealer was applied to securely cover the entire plate and interwell areas, and the plate was rotated at 37° C. for 1 hour. After incubation, the plate was centrifuged for 5 min at 100×g, the plate sealer was gently removed, and the plate surface was dried with a sterile cotton swab dipped in 70% ethanol. Fifty microliters was removed from each microtiter well and was added to individual wells of the 24 well quantitation plates which already contained the 0.4 ml/well of melted (38°–40° C.) 0.4% TSB/agarose. These plates were placed on a flatbed shaker for 1 min at 150 RPM and the agarose was allowed to harden for 15 min at RT. Finally, a 0.4 ml TSB/agarose overlay was added to each well, followed by a hardening period of 15 min at 4° C. before the plates were incubated overnight at 37° C. After 18 hours the colonies were enumerated and the data was reported as colony forming units (CFU) for each condition.

The bacterial serotypes used herein, except *K. pneumoniae*, were only inactivated in the presence of monoclonal antibody 7D7, an active complement source, and human neutrophils (Table 1). When this experiment was repeated with several non-7D7 reactive bacterial serotypes, no bacteria destruction was observed (data not shown), thus demonstrating the functional specificity of monoclonal antibody 7D7 and its capacity to opsonize bacteria and promote their phagocytosis. Since the combined actions of opsonins (specific antibodies) and polymorphonuclear leukocytes (neutrophils) appeared to be the primary mechanism for immunity to these bacterial strains, these data suggested that antibody 7D7, would, after appropriate administration, provide protection against lethal challenges with the bacteria serotypes described herein.

TABLE 1

| Bacteria | Neutrophils | Antibody | Complement | % Destruction of Input Bacteria |
|---|---|---|---|---|
| *E. coli* 08 and 075 | + | 7D7 | —[a] | 0 |
| *E. coli* 08 and 075 | + | 6F11[b] | + | 0 |
| *E. coli* 08 and 075 | − | 7D7 | + | 0 |
| *E. coli* 08 and 075 | + | 7D7 | + | 85% |
| *S. marcescens* 012 and 015 | + | 7D7 | − | 0 |
| *S. marcescens* 012 and 015 | + | 6F11 | + | 0 |
| *S. marcescens* 012 and 015 | − | 7D7 | + | 0 |
| *S. marcescens* 012 and 015 | + | 7D7 | + | 85% |
| *E. aerogenes* Isolates (2) | + | 7D7 | − | 0 |
| *E. aerogenes* Isolates (2) | + | 6F11 | + | 0 |
| *E. aerogenes* Isolates (2) | − | 7D7 | + | 0 |
| *E. aerogenes* Isolates (2) | + | 7D7 | + | 85% |

[a](−) = heat-inactivated (56° C. for 30 min) human complement.
[b](6F11) = culture supernatant containing an IgM human monoclonal antibody to *Pseudomonas aeruginosa* Fisher type 2.

H. In Vivo Activity

To test the above hypothesis, animal protection studies were performed with the 7D7 antibody and at least one organism from the *E. coli* and *E. aerogenes* species described herein. 7D7 and negative control (6F11, human IgM monoclonal antibody specific to *Pseudomonas aeruginosa* Fisher immunotype 2) antibodies were first concentrated from spent culture supernatants by precipitation with solid ammonium sulphate (50% final concentration) (Good, A. J. et al., "Purification of Immunoglobulins and Their Fragments," in *Selected Methods in Cellular Immunology*, Mishell, B. B. and Shiigi, S. M., eds., W. H. Freeman and Company, San Francisco, Calif. (1980) 279–286). Precipitated material was reconstituted in sterile water and extensively dialyzed against PBS.

The IgM antibody in the ammonium sulphate salt precipitate was purified by affinity chromatography on a murine monoclonal anti-human IgM antibody affinity column. To prepare the column, one gram of dehydrated cyanogen bromide activated Sepharose 4B (Pharmacia) was mixed with 15 ml ice cold 1 mM HCl in distilled water. The

19 hydrated gel was washed in 30 ml coupling buffer (0.1M carbonate (NaHCO₃) in 0.5M NaCl, pH 8.2), drained to form a moist cake and was combined with the ammonium salt precipitate dissolved in 1-3 ml of coupling buffer. The gel suspension was mixed end-over-end for 2 hr at RT and subsequently centrifuged at 200×g for 5 min. To block still available reactive sites, the supernatant was removed, 10 ml of 1M ethanolamine was added to the gel, and mixing was continued as above. The suspension was centrifuged at 200×g for 5 min and the supernatant was discarded. The gel was prepared for use with 1 wash in 0.1M acetate/saline buffer (6.8 g sodium acetate trihydrate and 14.6 g NaCl were dissolved in 500 ml distilled water containing 2.9 ml glacial acetic acid, pH 4.0), two washes in coupling buffer, and two washes in PBS. The gel was poured into a Pharmacia C10/10 column and stored at 4° C. until use.

To purify the immunoglobulin, 0.5 ml of salt fractionated material was diluted to 2.0 ml in PBS and was added to the affinity column. Following sample loading, the column was washed with PBS, pH 8.0 until the absorbancy monitor indicated no further protein in the flow-through. The bound antibody was eluted with 2 M MgCl₂ in PBS, the protein concentration was determined for each fraction at O.D.$_{280}$, and the peak fractions pooled. The antibody containing fraction was desalted on a G-25 Sephadex column and, if necessary, was con- centrated by microconcentration centrifugation (Centricon 30, Amicon Corp., Danver, Mass.) to 1-2 mg/ml. The final preparation was tested for purity by SDS-polyacrylamide gel electrophoresis followed by silver nitrate staining of proteins (Morrissey, J. H., "Silver Stain for Proteins in Polyacrylamide Gels: A Modified Procedure with Enhanced Uniform Sensitivity," Anal. Biochem., (1981) 117:307-310), and for antibody activity by ELISA as stated herein.

For each bacteria challenge, female, outbred Swiss-Webster mice weighing between 20 and 22 gm were divided into three groups of ten mice each. A representative experiment was performed as follows:

| Group | Bacteria | Antibody |
|---|---|---|
| A | E. coli O8 | 7D7 |
| B | E. coli O8 | 6F11 |
| C | S. marcescens O14 | 7D7 |

Each group receiving antibody was injected intravenously with 200 μl of sterile PBS containing 25 μg of purified antibody. Two hours later, all animals were challenged intraperitoneally with 300 μl of live bacteria containing 3 LD₅₀ of their respective bacterial strain. The bacterial suspension had been prepared from a broth culture in logarithmic phase growth, from which the bacteria was centrifuged, washed twice in PBS, and resuspended to the appropriate concentration in PBS. Animals were observed for a period of five days. Twenty-four to forty-eight hours post-challenge all animals in Group B (irrelevant antibody) and Group C (irrelevant organism) were dead. In contrast, those animals that had received the 7D7 (Group A) antibody were all alive and symptom free.

Animal protection models were used to test the protective effect of the 7D7 antibody against bacterial challenges with organisms belonging to the three genera stated in Table 1. A summary of the E. coli test data is presented in Table 2.

20

TABLE 2

| Challenge Bacteria | Antibody | Survival/Challenge | % Survival |
|---|---|---|---|
| E. coli O8 | 7D7 | 10/10 | 100 |
| E. coli O8 | 6F11[a] | 0/10 | 0 |
| S. marcescens O14[b] | 7D7 | 0/10 | 0 |

[a]6F11 antibody is specific to Pseudomonas aeruginosa Fisher immunotype 2 and serves as negative control antibody.
[b]S. Marcescens O14 is not reactive with the 7D7 antibody and serves as a nonspecific control organism.

TABLE 2a

| | % Survival[c] Day | | | | |
|---|---|---|---|---|---|
| Antibody | 0 | 1 | 2 | 3 | 4 |
| 6F11 | 12 | 2 | 2 | 1 | 1 |
| 7D7 | 12 | 10 | 6 | 4 | 4 |

[c]LD₅₀'s and protection studies were performed with mice rendered neutropenic by injection with cyclophosphamide as follows: Day 0 - 150 mg/kg, Day 2 - 50 mg/kg. On Day 4 mice received antibody and bacteria as described herein.

The data and data obtained with Enterobactor aerogenes demonstrate that the human monoclonal antibody 7D7 is able to protect mice from lethal challenges with bacteria belonging to two different gram-negative bacteria species. Because 7D7 is reactive with a carbohydrate epitope present on LPS, but LPS molecules on K. pneumoniae are less accessible (Orskov, I. and Orskov, F , "Serotyping of Klebsiella," in Methods in Microbiology, Vol. 14, Bergan, T., Ed., Academic Press, Orlando, Fla. (1984) 143–146) protection by the 7D7 antibody against K. pneumoniae infections was not evident (data not shown). Nor was the 7D7 antibody protective against a strain of Serratia marcescens tested (data not shown). Nonetheless, the intergenus cross-reactive human monoclonal antibody 7D7 was able to afford protection with 25 μg of purified antibody against infection by organisms belonging to the gram-negative bacteria species E. coli and E. aerogenes.

EXAMPLE II

Example II demonstrates methods for the production and selection of a human monoclonal antibody that possesses intergenus cross-reactivity against members of the species Serratia marcescens, Klebsiella pneumoniae and Enterobacter aerogenes. Further, this example demonstrates the in vitro opsonic activity of said antibody against homologous S. marcescens, K. pneumoniae, and E. aerogenes serotypes. The process of Example I (essentially as described in parts A through G) was repeated to produce a human monoclonal antibody that was cross-protective against infections caused by the bacteria described herein, except that it was necessary to make specific modifications to characterize and assay the antibody described in this Example. The following are changes in assay procedures and the results obtained with the monoclonal antibody described herein.

1. Culture supernatants from six transformations were analyzed by the above method resulting in the identification of one well (4F10) which possessed activity on the S. marcescens serotype plate, but not on the E. coli or control plate. It was determined in subsequent ELISA's with individual S. marcescens serotypes, that this well contained antibody reactive with the S. marcescens serotypes O15 and O18, but not any other of the twenty known S. marcescens LPS serotypes.

Prior to the filing of this patent application, the continuous transformed human cell line identified as 4F10 was deposited with the American Type Culture Collection, Rockville, Md. as A.T.C.C. No. CRL 9007.

2. Antibody from the cloned 4F10 cell line was assayed for further intergenus cross-reactivity by a modification of the standard immunoblotting technique. Specifically, cross-reactivity to the bacteria *K. pneumoniae, E. aerogenes,* and *E. cloacae* was investigated by spotting bacteria onto a gridded nitrocellulose paper disc, reacting the disc containing the bacteria with said antibody, and developing the antibody reactions with an alkaline phosphatase/nitroblue tetrazolium enzyme system.

From these experiments, the 4F10 antibody was observed to possess further intergenus cross-reactivity. This antibody reacted with the following serotypes:

| K. pneumoniae | S. marcescens | E. aerogenes |
| --- | --- | --- |
| K3,12,29,31,68,72 | O15,18 | Clinical Isolates |

Thus, the human monoclonal antibody 4F10 possessed intergenus cross-reactivity to bacteria belonging to the species *S. marcescens, K. pneumoniae, E. aerogenes*.

3. Using the immunoblot technique, positive reactions were noted in all tracks that contained deoxycholate extracts of the bacteria described herein. In these tracks, the 4F10 antibody appeared to recognize either a broad band of components or a series of regularly spaced molecular entities giving rise to a ladder-like pattern. This profile was entirely consistent with that seen in polyacrylamide gel electrophoretic analyses of carbohydrate moieties that demonstrate either extensive molecular weight heterogeneity due to an often repeating specific sugar sequence or to LPS molecules differing by weight increments equivalent to the number of O-antigenic oligosaccharide side chain units per molecule (Vimr, E. R., et al., "Use of Procaryotic-Derived Probes to Identify Poly (Sialic Acid) in Neonatal Neuronal Membranes," Proc. Natl. Acad. Sci., (1983) 81:1971–1975; and Holden, K. G. et al., "Gel Electrophoresis of Mucous Glycoproteins, I. Effect of Gel Porosity," Biochemistry (1971) 10:3105–3109). These data indicate that the monoclonal antibody 4F10 is directed against an antigenic determinant shared by carbohydrate molecules found on some serotypes of *S. marcescens, K. pneumoniae,* and *E. aerogenes*.

The immunoblot patterns observed after Proteinase K treatment were identical to those patterns observed without treatment and thus suggest that the antigen reactive with the 4F10 antibody is not protein in nature.

To specifically address whether 4F10 reacted with carbohydrate epitope, the electrotransferred deoxycholate sample was subjected to mild periodate oxidation prior to reacting the nitrocellulose paper with antibody. Electro-blotted deoxycholate extracts treated in this manner were no longer reactive with the 4F10 monoclonal antibody. These data strongly indicate that the epitope recognized by this antibody is a carbohydrate moiety present on molecules possessed by the bacteria described herein.

4. The isotype of the 4F10 monoclonal antibody was determined in an ELISA procedure similar to the specificity tests described in Example I except that the antigen plate contained a pool of PLL immobilized *S. marcescens* O15 and O18 serotypes. Positive reaction of the 4F10 monoclonal antibody with the *S. marcescens* serotypes was observed only with the anti-IgM reagent, demonstrating an IgM isotype for the monoclonal antibody. It will be appreciated by those skilled in the art that if the process of this example were repeated several times and the isotypes of intergenus cross-reactive monoclonal antibodies so obtained were determined, one would find additional isotypes, e.g., IgM and IgG isotypes.

5. In vitro functional activity of the 4F10 monoclonal antibody was examined in an opsonophagocytic assay which compared the bacteriocidal activity of the antibody in the presence and absence of both human neutrophils and human complement.

The bacterial serotypes used herein were only inactivated in the presence of monoclonal antibody 4F10, an active complement source, and human neutrophils (Table 3). When this experiment was repeated with several non-4F10 reactive bacterial serotypes, no bacterial destruction was observed (data not shown) thus demonstrating the functional specificity of monoclonal antibody 4F10 and its capacity to opsonize bacteria and promote their phagocytosis.

TABLE 3

| Bacteria | Neutrophils | Antibody | Complement | % Destruction of Input Bacteria |
| --- | --- | --- | --- | --- |
| S. marcescens O18 and O15 | + | 4F10 | −[a] | 0 |
| S. marcescens O18 and O15 | + | 6F11[b] | + | 0 |
| S. marcescens O18 and O15 | − | 4F10 | + | 0 |
| S. marcescens O18 and O15 | + | 4F10 | + | 85% |
| K. pneumoniae K3 and K12 | + | 4F10 | − | 0 |
| K. pneumoniae K3 and K12 | + | 6F11 | + | 0 |
| K. pneumoniae K3 and K12 | − | 4F10 | + | 0 |
| K. pneumoniae K3 and K12 | + | 4F10 | + | 60% |
| E. aerogenes Isolates (2) | + | 4F10 | − | 0 |
| E. aerogenes Isolates (2) | + | 6F11 | + | 0 |
| E. aerogenes Isolates (2) | − | 4F10 | + | 0 |
| E. aerogenes Isolates (2) | + | 4F10 | + | 85% |

[a](−) = heat-inactivated (56° C. for 30 min) human complement.
[b](6F11) = culture supernatant containing an IgM human monoclonal antibody to *Pseudomonas aeruginosa* Fisher type 2.

EXAMPLE III

Example III demonstrates methods for the production of a human monoclonal antibody that is reactive with both the *Escherichia coli* capsular type K1 and *Neisseria meningitidis* (*N. meningitidis*) Group B polysaccharide and further demonstrates the protective activity of said antibody in vivo against a lethal challenge of homologous *E. coli* and *N. meningitidis* bacterial species. The process of Example I (essentially described in parts A through G) was repeated to produce a human monoclonal antibody that was cross-protective against infections caused by the bacteria described herein, except that it was necessary to make specific modifications to characterize and assay the antibody described in this Example. The following are changes in assay procedures and the results obtained with the monoclonal antibody described herein.

1. Culture supernatants from five transformations were analyzed by the above method resulting in the identification of four wells (5D4, 2C10, 9B10, and 8A8) which contained anti- *E. coli* specificity on the *E. coli* serotype plate, but not on the *S. marcescens* or control plates. It was determined in subsequent ELISA's, conducted as set forth, on individual *E. coli* serotypes, that these wells contained antibody reactive with, at least, the *E. coli* serotypes: 01 (ATCC 23499), 07:K1 (ATCC 12792), 016:K1 (ATCC 23511), and 050 (CDC 1113-83), but not 04 (ATCC 12792), 06:K2 (ATCC 19138), 08:K8 (ATCC 23501), 09:K9 (ATCC 23505), or 022:K13 (ATCC 23517). Due to its better performance during the cloning procedure and increased antibody production, the 9B10 monoclonal antibody was selected for further analysis.

Prior to filing of this patent application the continuous transformed human cell line identified herein as 9B10 was deposited in the American Type Culture Collection, Rockville, Md. as A.T.C.C. No. CRL 9006.

2. The finding that the monoclonal antibodies from each of the clones reacted with the identical group of *E. coli* O-antigen serotypes, indicated that these antibodies were directed against a bacterial surface structure common to these serotypes. Several approaches were used to define the surface structure common to these *E. coli* serotypes. As set forth, two (07:K1 and 016:K1) of the four *E. coli* serotypes identified by the 9B10 antibody possessed the K1 capsular serotype, while the other two (01 and 050) had not been typed for their K-antigen serotype. Thus, the possibility was pursued that the 9B10 antibody contained reactivity to the K1 antigen and that the *E. coli* strains possessing the O-antigen serotypes 01 and 050 also possessed the K1 capsular serotype.

Others have taken advantage of the thermolability of the K1 capsule to establish its presence. Heating of K1 positive *E. coli* serotypes in a boiling water bath at 100° C. for 60 minutes removes the subsequent ability of these strains to react with anti-K1 sera and enhances their ability to react with anti-O antigen sera (Orskov, F. and Orskov, L., "Serotyping of *Escherichia coli*," in Methods in Microbiology, Vol. 14, T. Bergan, ed., Academic Press, London (1984) pp. 44–105). The reciprocal effects to boiling are most likely due to the removal of the capsule and the increased accessibility of antibody for lipopolysaccharide (LPS) molecules. The *E. coli* K1 positive serotypes (07 and 016) and the non-K1 typed serotypes (01 and 050) were heated as set forth and reacted with the 9B10 antibody and LPS serotype specific heterologous sera (Difco Bacto-*E. coli* Typing Reagents) in the ELISA procedure. Heat treated organisms lost all reactivity to the 9B10 antibody and had increased their reactivity with their homologous LPS serotype specific sera, while non-treated (control) organisms remained strongly reactive with 9B10 culture supernatants and poorly reactive with their respective LPS serotype specific antisera.

The polysaccharide (carbohydrate) from *Neisseria meningitidis* Group B bacteria (a homopolymer of sialic acid, alpha 2,8-linked poly-N-acetyl neuraminic acid) has been proven to be chemically and antigenically homogeneous with the *E. coli* K1 polysaccharide (Grados, O. and Ewing, W. H., "Antigenic Relationship between *Escherichia coli* and *Neisseria meningitidis*, "J. Immunol. (1973) 110:262–268). These data suggest that if the 9B10 monoclonal antibody contains specificity to *E. coli* K1 capsule then the antibody should also contain specificity to *N. meningitidis* Group B polysaccharide and further, that monoclonal antibodies containing specificity to the Group B polysaccharide of *N. meningitidis* should also demonstrate reactivity to *E. coli* strains possessing the K1 capsule. Two experimental protocols were used that tested for (1) the ability of the 9B10 antibody to react with *N. meningitidis* and (2) the ability of an antibody against *N. meningitidis* Group B polysaccharide to react with the four *E. coli* 9B10 reactive serotypes.

Highly purified Group B polysaccharide (Connaught Laboratories, Toronto, Canada) and viable *N. meningitidis* Group B bacteria were reacted with the 9B10 antibody in an ELISA as set forth. The 9B10 monoclonal antibody strongly reacted against both antigen preparations. To prove the converse specificity, a commercially available *N. meningitidis* Group B Meningitis Test Kit ("Directagen" Direct Antigen Detection System, Hynson, Westcott, and Dunning, Baltimore, Md.), that utilizes latex spheres coated with a murine monoclonal antibody to the Group B polysaccharide, was used. In agglutination assays using the 9B10 positive *E. coli* serotypes, all four serotypes demonstrated strong reactivity with the antibody coated spheres. *E. coli* serotypes known to be K1-antigen negative were also negative in this test system. Collectively, these data indicate that the 9B10 monoclonal antibody is reactive with the *E. coli* K1 capsule and the type-specific carbohydrate on *N. meningitidis* Group B. Further, since many of these assays were performed with intact, viable bacteria, it can be inferred that monoclonal antibody 9B10 is specific for some portion of an externally exposed region of the poly-sialic acid molecule.

3. The isotype of the 9B10 monoclonal antibody was determined in an ELISA procedure similar to the specificity tests described in Example I except that the antigen plate contained a pool of PLL immobilized *E. coli* K1 positive serotypes. Positive reaction of the 9B10 monoclonal antibody with the K1 positive *E. coli* serotypes was observed only with the anti-IgM reagent, demonstrating an IgM isotype for the monoclonal antibody. It will be appreciated by those skilled in the art that if the process of this Example were repeated several times and the isotypes of K1-specific monoclonal antibodies so obtained were determined, one would find additional isotypes, e.g., IgM and IgG isotypes.

4. In vitro functional activity of the 9B10 monoclonal antibody was examined in an opsonophagocytic assay which compared the bacteriocidal activity of the antibody in the presence and absence of both human neutrophils and human complement.

K1 positive *E. coli* serotypes were only inactivated in the presence of monoclonal antibody 9B10, an active complement source, and human neutrophils (Table 4). When this experiment was repeated with several K1 negative *E. coli* serotypes, no bacterial destruction assay was observed (data not shown) thus demonstrating the K1 specificity of monoclonal antibody 9B10 and its capacity to opsonize bacteria and promote their phagocytosis. Since the combined action of opsonins (specific antibodies) and polymorphonuclear leukocytes (neutrophils) appeared to be the primary mechanism for immunity to K1 positive *E. coli* serotypes, these data suggested that antibody 9B10, would, after appropriate administration, provide protection against a lethal challenge with any *E. coli* K1 encapsulated serotypes, regardless of its O-antigen serotype.

TABLE 4

| Bacteria | Neutrophils | Antibody | Complement | % Destruction of Input Bacteria |
|---|---|---|---|---|
| E. coli O1:K1 and O18:K1 | + | 9B10 | −[a] | 0 |
| E. coli O1:K1 and O18:K1 | + | 6F11[b] | + | 0 |
| E. coli O1:K1 and O18:K1 | − | 9B10 | + | 0 |
| E. coli O1:K1 and O18:K1 | + | 9B10 | + | 99% |
| N. meningitidis Group B | + | 9B10 | − | 0 |
| N. meningitidis Group B | + | 6F11 | + | 0 |
| N. meningitidis Group B | − | 9B10 | + | 0 |
| N. meningitidis Group B | + | 9B10 | + | 99% |

[a](−) = heat-inactivated (56° C.) for 30 min) human complement.
[b](6F11) = culture supernatant containing an IgM human monoclonal antibody to Pseudomonas aeruginosa Fisher type 2.

5. To test the above hypothesis, animal protection studies were performed with the 9B10 antibody and several K1 positive and K1 negative E. coli serotypes, as well as a N. meningitidis Group B serotype (strain H313, obtained from Dr. Carl Frasch, Laboratory of Bacterial Polysaccharides, Office of Biologics, Food and Drug Administration, Bethesda, Md.).

For each bacteria challenge, female, outbred Swiss-Webster mice weighing between 20 and 22 gm were divided into three groups of ten mice each. A representative experiment was performed as follows:

| Group | Bacteria | Antibody |
|---|---|---|
| A | E. coli K1 | 9B10 |
| B | E. coli K1 | 6F11 |
| C | E. coli K2 | 9B10 |

Each group receiving antibody was injected intravenously with 200 µl of sterile PBS containing 25 µg of purified antibody. Two hours later, all animals were challenged intraperitoneally with 300 µl of live bacteria containing 3 $LD_{50}$ of their respective bacterial strain. The bacterial suspension had been prepared from a broth culture in logarithmic phase growth, from which the bacteria was centrifuged, washed twice in PBS, and resuspended to the appropriate concentration in PBS. Animals were observed for a period of five days. Twenty-four to forty-eight hours post-challenge all animals in Group B (irrelevant antibody) and Group C (irrelevant organism) were dead. In contrast, those animals that had received the 9B10 (Group A) antibody were all alive and symptom free.

This animal protection model was used to demonstrate the therapeutic effect of the 9B10 antibody against bacterial challenges with organisms belonging to the two species stated herein. A summary of these data is presented in TabLe 5.

TABLE 5

| Challenge Bacteria | Antibody | Survival/Challenge | % Survival |
|---|---|---|---|
| E. coli K1 | 9B10 | 10/10 | 100% |
| E. coli K1 | 6F11[a] | 0/10 | 0% |
| E. coli K2[b] | 9B10 | 0/10 | 0% |
| N. meningitidis Group B | 9B10 | 5/5 | 100% |
| N. meningitidis Group B | 6F11 | 0/5 | 0% |
| E. coli K2 | 9B10 | 0/5 | 0% |

[a]6F11 antibody is specific to Pseudomonas aeruginosa Fisher immunotype 2 and serves as negative control antibody.
[b]E. coli K2 is not reactive with the 9B10 antibody and serves as nonspecific control organisms.

These data demonstrate that the human monoclonal antibody 9B10 is able to protect mice from lethal challenges with bacteria belonging to two different gram-negative bacterial species. The intergenus cross-protective antibody was able to passively protect against infection by organisms belonging to the gram-negative bacterial species E. coli and N. meningitidis Group B.

EXAMPLE IV

Example IV demonstrates methods for the production of a human monoclonal antibody that possesses intergenus cross-reactivity against members of the species Escherichia coli (E. coli), Enterobacter cloacae (E. cloacae) and Group B Stretococcus. Further this Example demonstrates an antibody cross-reactive with species belonging to the two main bacteria divisions; gram-negative (E. coli and E. cloacae) and gram-positive (Group B Streptococcus). Even further, this Example demonstrates the in vivo protective activity of said antibody against a lethal challenge of homologous E. coli, and Group B Streptococcus serotypes. The process of Example I (essentially described in parts A through G) was repeated to produce a human monoclonal antibody that was cross-protective against infections caused by the bacteria described herein, except that it was necessary to make specific modifications to characterize and assay the antibody described in this Example. The following are changes in assay procedures and the results obtained with the monoclonal antibody described herein.

1. Supernatants were screened for the presence of anti-Group B Streptococcus antibodies using an enzyme-linked immunosorbent assay (ELISA) technique as described in Example I. The antigen plates consisted of a series of flat-bottom 96-well Immunolon 2 microtiter plates, the wells of which contained mixtures of Group B Streptococci capsule types affixed to the well surfaces with poly-L-lysine (PLL). Various antigen plates used in the screen included: (1) a mixture of Group B Streptococcus types Ia (A.T.C.C. No. 12400), Ib (A.T.C.C. No. 12401), Ic (A.T.C.C. No. 27591); (2) a mixture of types II (A.T.C.C. No. 12973) and III (clinical isolate obtained from Dr. C. Wilson, Children's Orthopedic Hospital, Dept. Infectious Disease, Seattle, Wash.); and (3) a microtiter plate with no bacteria.

Culture supernatants from two transformations were analyzed by the above method resulting in the identification of one well (4B9) which possessed activity on both Group B Streptococcus typing plates, but not the control plates. It was determined in subsequent ELISA's with individual Group B Streptococcus types, that this well contained antibody reactive with all five reference typing strains.

Thus, in this experiment one cloned transformed human cell line was achieved which is continuous (immortal) and secretes a human monoclonal antibody to a determinant on the surface of the Group B Streptococcus types set forth.

Prior to filing of this patent application, the continuous transformed human cell line identified as 4B9 was deposited with the American Type Culture Collection, Rockville, Md. as A.T.C.C. No. CRL 9008.

2. Antibody from the cloned 4B9 cell line was assayed for cross-reactivity to gram-negative and gram-positive bacteria by a modification of the standard immunoblotting technique. Specifically, cross-reactivity to the bacteria E. coli, K. pneumoniae, S. marcescens, E. aerogenes, E. cloacae, Hemophilus influenzae, and Staphylococcus aureus was investigated by spotting bacteria onto a gridded nitrocellulose paper disc, reacting the disc containing the bacteria with said antibody, and developing the antibody reactions with an alkaline phosphatase/nitroblue tetrazolium enzyme system (as described in Example I).

From these experiments, the 4B9 antibody was observed to possess cross-reactivity with particular gram-negative bacterial species. This antibody reacted with the E. coli LPS serotypes 04, 07, 018, and 025, and the E. cloacae clinical isolates. Thus the human monoclonal antibody 4B9 possesses intergenus cross-reactivity between the gram-negative and gram-positive bacteria belonging to the species E. coli, E. cloacae, and Group B Streptococcus.

3. The finding that the monoclonal antibody cross-reacted with several different bacterial genera belonging to both gram-positive and gram-negative bacterial divisions, suggested the antibody was directed against a shared protein or carbohydrate. The biochemical characterization of the molecular species recognized by the 4B9 antibody was accomplished by immunoblot analysis. For analysis of the gram-negative genera, washed bacteria were extracted in deoxycholate as described in EXAMPLE I. For the gram-positive bacteria, 1.0 L of bacteria cultured for 6 hours in modified Todd-Hewitt Broth (Difco, Todd-Hewitt Broth containing 2.8 gm/L anhydrous sodium phosphate, pH 7.8) at 37° C. were harvested by centrifugation and washed three times in PBS. The bacteria were resuspended in 85 ml of protoplast medium (40% sucrose w/v in 0.03M potassium phosphate buffer, pH 6.8 containing 10 mM $MgCl_2$) and the suspension was warmed to 37° C. for 10 min. Approximately 3000 units of the mutanolysin (SIGMA) were added and the mixture was shaken at 37° C. for 90 min or until the $OD_{660}$ of the suspension had been reduced by >90%. The digested material was centrifuged at 2000×g for 15 min at RT and the supernatant was dialyzed against PBS for 48 hr (Young, M. K. and Mattingly, S. J., "Biosynthesis of Cell Wall Peptidoglycan and Polysaccharide Antigens by Protoplasts of Type III Group B Streptococcus," J. Bact., (1983) 154:211–220). The dialysate was concentrated ten-fold by positive pressure dialysis through a PM-10 filter (Amicon Corp., Danvers, Mass.).

Carbohydrates binding to wheat germ agglutinin were purified by affinity chromatography on a wheat germ lectin Sepharose 6MB column (SIGMA). The bound digest, described herein, was eluted from the column with 10 ml of 0.1M N-acetylglucosamine and the eluate was dialyzed against distilled water at 4° C. The affinity purified eluate was dried by lyophilization and the dry weight of the resulting material was obtained (Gray, B. M., et al., "Interaction of Group B Streptococcal Type-Specific Polysaccharides with Wheat Germ Agglutinin and Other Lectins," J. or Immunol. Meth., (1984) 72:269–277). Positive reactions were noted in all tracks that contained deoxycholate extracts of the bacteria described herein. In those tracks containing extracts from gram-negative bacteria, the 4B9 antibody appeared to recognize a series of regularly spaced molecular entities giving rise to a ladder-like pattern on the immunoblot. This profile was entirely consistent with that seen in polyacrylamide gel electrophoretic analysis of LPS in the presence of SDS, where it has been demonstrated that the heterogenous size profile exhibited by the bands is due to a population of LPS molecules differing by weight increments equivalent to the number of O-antigenic oligosaccharide side chain units present per molecule (Pavla, E. T. and Makela, P. H., supra and Goldman, R. D. and Leive, L., supra). In those tracks containing extracts from the Group B Streptococcus types, the 4B9 antibody appeared to recognize components present on a broad band. This profile was consistent with that seen in polyacrylamide gel electrophoresis analyses of carbohydrate moieties that demonstrate extensive molecular weight heterogeneity with a frequently repeating specific sugar sequence (Vmir, E. R. et al., supra and Holden, K. G., supra). These data indicate that the monoclonal antibody 4B9 is directed against an antigenic determinant shared by molecules found on some serotypes of E. coli, E. cloacae, and Group B Streptococcus.

To further define the molecular nature of the antigen, the deoxycholate extracts were treated with proteolytic enzyme Proteinase K prior to their electrophoresis (Eberling, W., supra). The immunoblot patterns observed after Proteinase K treatment were identical to those patterns observed without treatment and thus suggest that the antigen reactive with the 4B9 antibody is not protein in nature.

To specifically address whether 4B9 reacted with a carbohydrate epitope, the electrotransferred deoxycholate and wheat germ agglutination affinity purified samples were subjected to mild periodate oxidation prior to reacting the nitrocellulose paper with antibody (see EXAMPLE I). Electro-blotted deoxycholate extracts treated in this manner were no longer reactive with the 4B9 monoclonal antibody. These data strongly indicate that that epitope recognized by this antibody is a carbohydrate moiety present in molecules possessed by both the gram-negative and gram-positive bacteria described herein.

4. The isotype of the 4B9 monoclonal antibody was determined in an ELISA procedure similar to the specificity tests described above except that the antigen plate contained a pool of PLL immobilized Group B Streptococcus types II and III. Positive reaction of the 4B9 monoclonal antibody with the Group B streptococcus strains was observed only with the anti-IgM reagent, demonstrating an IgM isotype for the monoclonal antibody.

5. In vitro functional activity of the 4B9 monoclonal antibody was examined in an opsonophagocytic assay which compared the bacteriocidal activity of the antibody in the presence and absence of both human neutrophils and human complement.

The bacterial strains used herein were only inactivated in the presence of monoclonal antibody 4B9, an active complement source, and human neutrophils (Table 6). When this experiment was repeated with several non-4B9 reactive bacterial serotypes, no bacteria destruction was observed (data not shown) thus demonstrating the functional specificity of monoclonal antibody 4B9 and its capacity to opsonize bacteria and promote their phagocytosis. Since the combined actions of opsonins (specific antibodies) and polymorphonuclear leukocytes (neutrophils) appeared to be the primary mechanism for immunity to these bacterial strains, these data suggest that antibody 4B9, would, after appropriate administration, provide protection against lethal challenges with the bacteria strains described herein.

TABLE 6

| Bacteria | Neutrophils | Antibody | Complement | % Destruction of Input Bacteria |
|---|---|---|---|---|
| E. coli 018 and 025 | + | 4B9 | −[a] | 0 |
| E. coli 018 and 025 | + | 6F11[b] | + | 0 |
| E. coli 018 and 025 | − | 4B9 | + | 0 |
| E. coli 018 and 025 | + | 4B9 | + | 85% |
| E. cloacae Isolates | + | 4B9 | − | 0 |
| E. cloacae Isolates | + | 6F11 | + | 0 |
| E. cloacae Isolates | − | 4B9 | + | 0 |
| E. cloacae Isolates | + | 4B9 | + | 85% |
| Group B. Strep. Types Ia and III | + | 4B9 | − | 0 |
| Group B. Strep. Types Ia and III | + | 6F11 | + | 0 |
| Group B. Strep. Types Ia and III | − | 4B9 | + | 0 |
| Group B. Strep. Types Ia and III | + | 4B9 | + | 85% |

[a](−) = heat-inactivated (56° C. for 30 min) human complement.
[b](6F11) = culture supernatant containing an IgM human monoclonal antibody to Pseudomonas aeruginosa Fisher type 2.

6. To test the above hypothesis, animal protection studies were performed with the 4B9 antibody and at Least one organism from each genus described herein.

From each gram-negative bacteria challenge, female, outbred Swiss-Webster mice weighing between 20 and 22 gm were divided into three groups of ten mice each. A representative experiment was performed as follows:

| Group | Bacteria | Antibody |
|---|---|---|
| A | E. coli 018 | 4B9 |
| B | E. coli 018 | 6F11 |
| C | S. marcescens 014 | 4B9 |

Each group receiving antibody was injected intravenously with 200 μl of sterile PBS containing 25 μg of purified antibody. Two hours later, all animals were challenged intraperitoneally with 300 μl of live bacteria containing 3 $LD_{50}$ of their respective bacterial strain. The bacterial suspension had been prepared from a broth culture in logarithmic phase growth, from which the bacteria was centrifuged, washed twice in PBS, and resuspended to the appropriate concentration in PBS. Animals were observed for a period of five days. Twenty-four to forty-eight hours post-challenge all animals Group B (irrelevant antibody) and Group C (irrelevant organism) were dead. In contrast, those animals that had received the 4B9 (Group A) antibody were all alive and symptom free.

For the Group B Streptococcus protection studies, a neonatal rat model was used. Outbred Sprague-Dawley rat pups (housed with their mothers), less than 48 hours old received antibody and bacteria essentially as described for the mouse protection studies. Primary differences were as follows: 1) both the antibodies and bacterial challenges were injected intraperitoneally, and 2) the inoculum size was reduced to 20 μl.

These animal protection models were used to demonstrate the therapeutic effect of the 4B9 antibody against bacterial challenges with organisms belonging to two of the three species stated herein. A summary of these data is presented in Table 7.

TABLE 7

| Challenge Bacteria | Antibody | Survival/Challenge | % Survival |
|---|---|---|---|
| E. coli 025 | 4B9 | 10/10 | 100 |
| E. coli 025 | 6F11[a] | 0/10 | 0 |
| S. marcescens 014[b] | 4B9 | 0/10 | 0 |
| Group B Streptococcus Ia and III | 4B9 | 10/10 | 100 |
| Group B Streptococcus Ia and III | 6F11 | 0/10 | 0 |
| S. marcescens 014 | 9B10 | 0/10 | 0 |

[a]6F11 antibody is specific to Pseudomonas aeruginosa Fisher immunotype 2 and serves as negative control antibody.
[b]S. marcescens 014 is not reactive with the 4B9 antibody and serve as a non-specific control organisms.

These data demonstrate that the human monoclonal antibody 4B9 is able to protect mice and rats from lethal challenges with bacteria genera belonging to both gram-negative and gram-positive bacterial divisions. The intergenus cross-reactive human monoclonal antibody 4B9 was able to afford protection with 25 μg of purified antibody against infection by organisms belonging to the gram-negative bacteria genera E. coli and the gram-positive bacteria belonging to Group B Streptococcus.

EXAMPLE V

EXAMPLE V demonstrates methods for the production and selection of a human monoclonal antibody that possesses intergenus cross-reactivity against members of the genera Serratia marcescens, Klebsiella pneumoniae, and Enterobacter aerogenes. Further, this example demonstrates the in vitro opsonic activity of said antibody against homologous S. marcescens, K. pneumoniae, and E. aerogenes serotypes. The process of Example I (essentially as described in parts A through G) was repeated, except that it was necessary to make specific modifications to characterize and assay the antibody described in this Example. The following are changes in assay procedures and the results obtained with the monoclonal antibody described herein.

1. Culture supernatants from four transformations were analyzed by the above method resulting in the identification of one well (7E10) which possessed binding activity on at least one of four K. pneumoniae serotype plates, containing the capsule serotypes; 1, 2, 3, 4, 6, 8, 9, 19, 20, 21, 24, 27, 31, 43, 44, and 55, but not on the control plate (no bacteria). Antibody from the 7E10 cell line was assayed for further intergenus cross-reactivity by a modification of the standard immunoblotting technique. Specifically, cross-reactivity to the bacteria K. pneumoniae, E. aerogenes, S. marcescens, E. coli, and P. aeruginosa was investigated by spotting bacteria onto a gridded nitrocellulose paper disc, reacting the disc containing the bacteria with said antibody, and developing the antibody reactions with an alkaline phosphatase/nitroblue tetrazolium enzyme system.

From these experiments, the 7E10 antibody was observed to possess further intergenus cross-reactivity. This antibody reacted with the following species and serotypes:

| K. pneumoniae | S. marcescens | E. aerogenes |
|---|---|---|
| K2,8,11,12,13,21, 26,29,30,33,42,68,69 | 04,12 | Clinical Isolates |

Thus, the human monoclonal antibody 7E10 possessed intergenus cross-reactivity to bacteria belonging to the genera K. pneumoniae, S. marcescens, and E. aerogenes.

2. The isotype of the 7E10 monoclonal antibody was determined in an ELISA procedure similar to the specificity tests described in Example I except that the antigen plate contained a pool of PLL (poly-L-lysine) immobilized K. pneumoniae K8 and K11 serotypes. Positive reaction of the 7E10 monoclonal antibody with the K. pneumoniae serotypes was observed only with the anti-IgM reagent, demonstrating an IgM isotype for the monoclonal antibody. It will be appreciated by those skilled in the art that if the process of this Example were repeated several times and the isotypes of intergenus cross-reactive monoclonal antibodies so obtained were determined, one would find additional isotypes, e.g., IgM and IgG isotypes.

3. In vitro functional activity of the 7E10 monoclonal antibody was examined in an opsonophagocytic assay which compared the bacteriocidal activity of the antibody in the presence and absence of both human neutrophils and human complement. The bacterial serotypes used herein were only inactivated in the presence of monoclonal antibody 7E10, an active complement source, and human neutrophils (Table 8). When this experiment was repeated with serotypes unreactive with antibody 7E10, no bacterial destruction was observed (data not shown). These experiments demonstrated the functional specificity of monoclonal antibody 7E10, as well as its capacity to opsonize bacteria and promote their phagocytosis.

TABLE 8

| Bacteria | Neutrophils | Antibody | Complement | % Destruction of Input Bacteria |
|---|---|---|---|---|
| S. marcescens 012 | + | 7E10 | −[a] | 0 |
| S. marcescens 012 | + | 6F11[b] | + | 0 |
| S. marcescens 012 | − | 7E10 | + | 0 |
| S. marcescens 012 | + | 7E10 | + | 86% |
| K. pneumoniae K8 and K11 | + | 7E10 | − | 0 |
| K. pneumoniae K8 and K11 | + | 6F11 | + | 0 |
| K. pneumoniae K8 and K11 | − | 7E10 | + | 0 |
| K. pneumoniae K8 and K11 | + | 7E10 | + | 94% |
| E. aerogenes Isolates | + | 7E10 | − | 0 |
| E. aerogenes Isolates | + | 6F11 | + | 0 |
| E. aerogenes Isolates | − | 7E10 | + | 0 |
| E. aerogenes Isolates | + | 7E10 | + | 60% |

[a] and [b] = see Table 3 footnotes

EXAMPLE VI

EXAMPLE VI demonstrates methods for the production and selection of a human monoclonal antibody that possesses intergenus cross-reactivity against members of the genera Serratia marcescens and Klebsiella pneumoniae. Further, this example demonstrates the in vitro opsonic activity of said antibody against homologous S. marcescens and K. pneumoniae serotypes. The process of Example I (essentially as described in parts A through G) was repeated, except that it was necessary to make specific modifications to characterize and assay the antibody described in this Example. The following are changes in assay procedures and the results obtained with the monoclonal antibody described herein.

1. Culture supernatants from four transformations were analyzed by the above method resulting in the identification of one well (8C9) which possessed binding activity on at least one of four K. pneumoniae serotype plates, containing the capsule serotypes: 1, 2, 3, 4, 6, 8, 9, 19, 20 21, 24 27, 31, 43, 44, and 55, but not on the control plate (no bacteria). Antibody from the 8C9 cell line was assayed for further intergenus cross-reactivity by a modification of the standard immunoblotting technique. Specifically, cross-reactivity to the bacteria K. pneumoniae, E. aerogenes, S. marcescens, E. coli, and P. aeruginosa was investigated by spotting bacteria onto a gridded nitrocellulose paper disc, reacting the disc containing the bacteria with said antibody, and developing the antibody reactions with an alkaline phosphatase/nitroblue tetrazolium enzyme system.

From these experiments, the 8C9 antibody was observed to possess further intergenus cross-reactivity. This antibody reacted with the following species and serotypes:

| K. pneumoniae | S. marcescens |
|---|---|
| K5,6,7,14,27,36,55,64 | 03 |

Thus, the human monoclonal antibody 8C9 possessed intergenus cross-reactivity to bacteria belonging to the genera K. pneumoniae and S. marcescens.

2. The isotype of the 8C9 monoclonal antibody was determined in an ELISA procedure similar to the specificity tests described in Example I except that the antigen plate contained a pool of PLL immobilized K. pneumoniae K14 and K27 serotypes. Positive reaction of the 8C9 monoclonal antibody with the K. pneumoniae serotypes was observed only with the anti-IgM reagent, demonstrating an IgM isotype for the monoclonal antibody. It will be appreciated by those skilled in the art that if the process of this example were repeated several times and the isotypes of intergenus cross-reactive monoclonal antibodies so obtained were determined, one would find additional isotypes, e.g., IgM and IgG isotypes.

3. In vitro functional activity of the 8C9 monoclonal antibody was examined in an opsonophagocytic assay which compared the bacteriocidal activity of the antibody in the presence and absence of both human neutrophils and human complement. The bacterial serotypes used herein were only inactivated in the presence of monoclonal antibody 8C9, an active complement source, and human neutrophils (Table 9). When this experiment was repeated with serotypes unreactive with antibody 8C9, no bacterial destruction was observed (data not shown). These experiments demonstrated the functional specificity of monoclonal antibody 8C9, as well as its capacity to opsonize bacteria and promote their phagocytosis.

TABLE 9

| Bacteria | Neutrophils | Antibody | Complement | % Destruction of Input Bacteria |
|---|---|---|---|---|
| S. marcescens O3 | + | 8C9 | −[a] | 0 |
| S. marcescens O3 | + | 6F11[b] | + | 0 |
| S. marcescens O3 | − | 8C9 | + | 0 |
| S. marcescens O3 | + | 8C9 | + | 70% |
| K. pneumoniae K14 and 27 | + | 8C9 | − | 0 |
| K. pneumoniae K14 and 27 | + | 6F11 | + | 0 |
| K. pneumoniae K14 and 27 | − | 8C9 | + | 0 |
| K. pneumoniae K14 and 27 | + | 8C9 | + | 93% |

[a] and [b] = see Table 3 footnotes

EXAMPLE VII

EXAMPLE VII demonstrates methods for the production and selection of a human monoclonal antibody that possesses intergenus cross-reactivity against members of the genera *Serratia marcescens*, *Klebsiella pneumoniae*, *Enterobacter aerogenes*, and *Enterobacter cloacae*. Further, this example demonstrates the in vitro opsonic activity of said antibody against homologous *S. marcescens*, *K. pneumoniae*, *E. aerogenes*, and *E. cloacae* serotypes. The process of Example I (essentially as described in parts A through G) was repeated, except that it was necessary to make specific modifications to characterize and assay the antibody described in this Example. The following are changes in assay procedures and the results obtained with the monoclonal antibody described herein.

1. Culture supernatants from four transformations were analyzed by the above method resulting in the identification of one well (1E4) which possessed binding activity on at least one of four *K. pneumoniae* serotype plates, containing the capsule serotypes: 1, 2, 3, 4, 6, 8, 9, 19, 20, 21, 24 27, 31, 43, 44, and 55, but not on the control plate (no bacteria). Antibody from the 1E4 cell line was assayed for further intergenus cross-reactivity by a modification of the standard immunoblotting technique. Specifically, cross-reactivity to the bacteria *K. pneumoniae*, *E. aerogenes*, *S. marcescens*, *E. coli*, *E. cloacae*, and *P. aeruginosa* was investigated by spotting bacteria onto a gridded nitrocellulose paper disc, reacting the disc containing the bacteria with said antibody, and developing the antibody reactions with an alkaline phosphatase/nitroblue tetrazolium enzyme system.

From these experiments, the 1E4 antibody was observed to possess further intergenus cross-reactivity. This antibody reacted with the following species and serotypes:

| K. pneumoniae | S. marcescens | E. aerogenes | E. cloacae |
|---|---|---|---|
| K1,3,8,9,13, 15,29,31,33,36, 68,69 | O15 | Clinical Isolates | Clinical Isolates |

Thus, the human monoclonal antibody 1E4 possessed intergenus cross-reactivity to bacteria belonging to the species *K. pneumoniae*, *S. marcescens*, *E. cloacae* and *E. aerogenes*.

2. The isotype of the 1E4 monoclonal antibody was determined in an ELISA procedure similar to the specificity tests described in Example I except that the antigen plate contained a pool of PLL immobilized *K. pneumoniae* K3 and K8 serotypes. Positive reaction of the 1E4 monoclonal antibody with the *K. pneumoniae* serotypes was observed only with the anti-IgM reagent, demonstrating an IgM isotype for the monoclonal antibody. It will be appreciated by those skilled in the art that if the process of this example were repeated several times and the isotypes of intergenus cross-reactive monoclonal antibodies so obtained were determined, one would find additional isotypes, e.g., IgM and IgG isotypes.

3. In vitro functional activity of the 1E4 monoclonal antibody was examined in an opsonophagocytic assay which compared the bacteriocidal activity of the antibody in the presence and absence of both human neutrophils and human complement. The bacterial serotypes used herein were only inactivated in the presence of monoclonal antibody 1E4, an active complement source, and human neutrophils (Table 10). When this experiment was repeated with serotypes unreactive with antibody 1E4, no bacterial destruction was observed (data not shown). These experiments demonstrated the functional specificity of monoclonal antibody 1E4, as well as its capacity to opsonize bacteria and promote their phagocytosis.

TABLE 10

| Bacteria | Neutrophils | Antibody | Complement | % Destruction of Input Bacteria |
|---|---|---|---|---|
| S. marcescens O15 | + | 1E4 | −[a] | 0 |
| S. marcescens O15 | + | 6F11[b] | + | 0 |
| S. marcescens O15 | − | 1E4 | + | 0 |
| S. marcescens O15 | + | 1E4 | + | 86% |
| K. pneumoniae K3 and 29 | + | 1E4 | − | 0 |
| K. pneumoniae K3 and 29 | + | 6F11 | + | 0 |
| K. pneumoniae K3 and 29 | − | 1E4 | + | 0 |
| K. pneumoniae K3 and 29 | + | 1E4 | + | 80% |
| E. aerogenes Isolate (2) | + | 1E4 | − | 0 |
| E. aerogenes Isolate (2) | + | 6F11 | + | 0 |
| E. aerogenes Isolate (2) | − | 1E4 | + | 0 |
| E. aerogenes Isolate (2) | + | 1E4 | + | 80% |
| E. cloacae Isolate | + | 1E4 | − | 0 |
| E. cloacae Isolate | + | 6F11 | + | 0 |
| E. cloacae Isolate | − | 1E4 | + | 0 |
| E. cloacae Isolate | + | 1E4 | + | 80% |

[a] and [b] = see Table 3 footnotes

EXAMPLE VIII

EXAMPLE VIII demonstrates methods for the production and selection of a human monoclonal antibody that possesses intergenus cross-reactivity against members of the genera *Serratia marcescens*, *Klebsiella pneumoniae*,

*Enterobacter aerogenes,* and *Pseudomonas aeruginosa.* Further, this example demonstrates the in vitro opsonic activity of said antibody against homologous *S. marcescens, K. pneumoniae, E. aerogenes,* and *P. aeruginosa* serotypes. The process of Example I (essentially as described in parts A through G) was repeated, except that it was necessary to make specific modifications to characterize and assay the antibody described in this Example. The following are changes in assay procedures and the results obtained with the monoclonal antibody described herein.

1. Culture supernatants from four transformations were analyzed by the above method resulting in the identification of one well (9D1) which possessed binding activity on at least one of four *K. pneumoniae* serotype plates, containing the capsule serotypes; 1, 2, 3, 4, 6, 8, 9, 19, 20, 24, 27, 31, 43, 44, and 55, but not on the control plate (no bacteria). Antibody from the 9D1 cell line was assayed for further intergenus cross-reactivity by a modification of the standard immunoblotting technique. Specifically, cross-reactivity to the bacteria *K. pneumoniae, E. aerogenes, S. marcescens, E. coli,* and *P. aeruginosa* was investigated by spotting bacteria onto a gridded nitrocellulose paper disc, reacting the disc containing the bacteria with said antibody, and developing the antibody reactions with an alkaline phosphatase/nitroblue tetrazolium enzyme system.

From these experiments, the 9D1 antibody was observed to possess further intergenus cross-reactivity. This antibody reacted with the following species and serotypes:

| K. pneumoniae | S. marcescens | E. aerogenes | P. aeruginosa |
|---|---|---|---|
| B9,13,15,29, 33 | 03,9,15,18 | Clinical Isolates | F6 |

Thus, the human monoclonal antibody 9D1 possessed intergenus cross-reactivity to bacteria belonging to the genera *K. pneumoniae, S. marcescens, E. aerogenes,* and *P. aeruginosa.*

2. The isotype of the 9D1 monoclonal antibody was determined in an ELISA procedure similar to the specificity tests described in Example I except that the antigen plate contained a pool of PLL immobilized *K. pneumoniae* K13 serotype. Positive reaction of the 9D1 monoclonal antibody with the *K. pneumoniae* serotypes was observed only with the anti-IgM reagent, demonstrating an IgM isotype for the monoclonal antibody. It will be appreciated by those skilled in the art that if the process of this example were repeated several times and the isotypes of intergenus cross-reactive monoclonal antibodies so obtained were determined, one would find additional isotypes, e.g., IgM and IgG isotypes.

3. In vitro functional activity of the 9D1 monoclonal antibody was examined in an opsonophagocytic assay which compared the bacteriocidal activity of the antibody in the presence and absence of both human neutrophils and human complement. The bacterial serotypes used herein were only inactivated in the presence of monoclonal antibody 9D1, an active complement source, and human neutrophils (Table 11). When this experiment was repeated with serotypes unreactive with antibody 9D1, no bacterial destruction was observed (data not shown). These experiments demonstrated the functional specificity of monoclonal antibody 9D1, as well as its capacity to opsonize bacteria and promote their phagocytosis.

TABLE 11

| Bacteria | Neutrophils | Antibody | Complement | % Destruction of Input Bacteria |
|---|---|---|---|---|
| S. marcescens 03 | + | 9D1 | –[a] | 0 |
| S. marcescens 03 | + | 6F11[b] | + | 0 |
| S. marcescens 03 | – | 9D1 | + | 0 |
| S. marcescens 03 | + | 9D1 | + | 87% |
| K. pneumoniae K13 | + | 9D1 | – | 0 |
| K. pneumoniae K13 | + | 6F11 | + | 0 |
| K. pneumoniae K13 | – | 9D1 | + | 0 |
| K. pneumoniae K13 | + | 9D1 | + | 50% |
| E. aerogenes Isolates (2) | + | 9D1 | – | 0 |
| E. aerogenes Isolates (2) | + | 6F11 | + | 0 |
| E. aerogenes Isolates (2) | – | 9D1 | + | 0 |
| E. aerogenes Isolates (2) | + | 9D1 | + | 70% |
| P. aeruginosa F6 | + | 9D1 | – | 0 |
| P. aeruginosa F6 | + | 6F11 | + | 0 |
| P. aeruginosa F6 | – | 9D1 | + | 0 |
| P. aeruginosa F6 | + | 9D1 | + | 75% |

[a] and [b] = see Table 3 footnotes

EXAMPLE IX

EXAMPLE IX demonstrates methods for production of a human monoclonal antibody that possesses intergenus cross-reactivity against members of the species *Pseudomonas aeruginosa (P. aeruginosa), Escherichia coli (E. coli),* and *Serratia marcescens (S. marcescens).* Further, this Example demonstrates the in vivo protective activity of said antibody against a lethal challenge of homologous *P. aeruginosa, E. coli,* and *S. marcescens* serotypes. The process of Example I (essentially as described in parts A through G) was repeated to produce a human monoclonal antibody that was cross-protective against infections caused by the bacteria to which it binds. Specific modifications to the process of Example I, to characterize and assay the antibody, are described in this Example. The changes in assay procedures and the results obtained with the monoclonal antibody were as follows.

1. Supernatants were screened for the presence of anti-*P. aeruginosa* antibodies using an ELISA technique as described in Example I. The antigen plate consisted of a flat-bottom 96-well Immunolon 2 microtiter plate (Dynatech, Alexandria, Va.), the wells of which contained a mixture of poly-L-lysine (PLL) immobilized bacteria belonging to the seven *P. aeruginosa* Fisher reference strains (Fisher, M. W., et al., *J. of Bacteriology* (1969) 98:835–836, A.T.C.C. Nos. 27312–27318).

Culture supernatants from one transformation were analyzed by the above method and resulted in the identification of one well that possessed activity on the *P. aeruginosa* plate, but not the PLL control plate. It was determined in subsequent ELISA's with the seventeen individual *P.*

*aeruginosa* serotypes belonging to the International Antigenic Typing Scheme (IATS, A.T.C.C. Nos. 33348–33364), that one master well 9C3 contained antibodies which bound to IATS serotype type 1 (Liu, P. V., *Int. J. Syst. Bacteriol.* (1983) 33:256–264, which is incorporated herein by reference).

Thus, from this experiment, one cloned transformed human cell line was achieved which is continuous (immortal) and secretes a single human monoclonal antibody which binds to a determinant on the surface of the *P. aeruginosa* IATS type 1.

Prior to filing this patent application, the continuous transformed human cell line identified as 9C3 was deposited with the American Type Culture Collection, Rockville, Md., at A.T.C.C. No. CRL 9239.

2. Antibody from the cloned 9C3 cell line was also assayed for cross-reactivity to gram-negative and gram-positive bacteria by a modification of the standard immunoblotting technique. Specifically, cross-reactivity to the bacteria *E. coli*, *K. pneumoniae*, *S. marcescens*, *E. aerogenes*, *E. cloacae*, *Haemophilus influenzae*, and *Staphylococcus aureus* was investigated by spotting bacteria onto a gridded nitrocellulose paper disc, reacting the disc containing the bacteria with 9C3 antibody, and visualizing the antibody reactions with an alkaline phosphatase/nitroblue tetrazolium enzyme system (as described in Example I).

From these experiments, antibody 9C3 was observed to bind to *E. coli* serotype 06 and the *S. marcescens* serotypes 012 and 014. Thus, the human mono- clonal antibody 9C3 possesses intergenus cross-reactivity among the gram-negative bacteria belonging to specific serotypes of the species *E. coli*, *S. marcescens*, and *P. aeruginosa*.

3. The finding that the monoclonal antibody cross-reacted with several different bacterial genera, suggested the antibody may bind to a shared antigenic determinant. The biochemical characterization of the molecular species recognized by the 9C3 antibody was accomplished by immunoblot analysis as described in Example I. Reactions were noted in deoxycholate extracts of reactive serotypes from *P. aeruginosa* and *E. coli*, but not *S. marcescens*. Although it is not clear why antibody 9C3 was unreactive with the *S. marcescens* preparation, it is possible the antibody recognizes a conformational epitope that was destroyed by the preparation treatments. For the *E. coli* and *P. aeruginosa* bacterial extracts, the 9C3 antibody appeared to recognize a series of regularly spaced molecular entities giving rise to a ladder-like pattern on the immunoblot. This profile was entirely consistent with that seen in polyacrylamide gel electrophoretic analysis of LPS in the presence of SDS, where it has been demonstrated that the heterogeneous size profile exhibited by the bands is due to a population of LPS molecules differing by weight increments equivalent to the number of O-antigenic oligosaccharide side chain units present per molecule (Pavla, E. T., and Makela, P. H., supra, and Goldman, R. D., and Leive, L., supra).

To further define the molecular nature of the antigen, the deoxycholate extracts were treated with proteolytic enzyme, Proteinase K, prior to their electrophoresis (Eberling, W., supra). The immunoblot patterns observed after Proteinase K treatment were identical to those patterns observed without treatment and, thus, suggested that the antigen reactive with the 9C3 antibody was not protein in nature.

4. The isotype of the 9C3 monoclonal antibody was determined in an ELISA procedure similar to the specificity tests described above, except that the antigen plate contained PLL-immobilized *P. aeruginosa* Fisher serotype 4 bacteria. Positive reaction of the 9C3 monoclonal antibody with the *P. aeruginosa* strain was observed only with the anti-IgM reagent, demonstrating an IgM isotype for the monoclonal antibody.

5. In vitro functional activity of the 9C3 monoclonal antibody was examined in an opsonophagocytic assay which compared the bacteriocidal activity of the antibody in the presence and absence of both human neutrophils and human complement.

The bacterial strains used herein were only killed in the presence on monoclonal antibody 9C3, an active complement source, and human neutrophils (Table 12). When this experiment was repeated with several non-9C3 reactive bacterial serotypes, no bacterial destruction was observed, thus demonstrating the functional specificity of monoclonal antibody 9C3 and its capacity to opsonize bacteria and promote their phagocytosis. Since the combined action of opsonins (specific antibodies) and polymorphonuclear leukocytes (neutrophils) appeared to be the primary mechanism for immunity to these bacterial strains, these data indicate that antibody 9C3 would, after appropriate administration, provide protection against lethal challenges with the bacteria strains described herein.

TABLE 12

| Bacteria | Neutro-phils | Antibody | Complement | % Destruction of Input Bacteria |
|---|---|---|---|---|
| *E. coli* 06 | + | 9C3 | −[a] | 0 |
| *E. coli* 06 | + | 6F11[b] | + | 0 |
| *E. coli* 06 | − | 9C3 | + | 0 |
| *E. coli* 06 | + | 9C3 | + | 98% |
| *S. marcescens* 014 | + | 9C3 | − | 0 |
| *S. marcescens* 014 | + | 6F11 | + | 0 |
| *S. marcescens* 014 | − | 9C3 | + | 0 |
| *S. marcescens* 014 | + | 9C3 | + | 94% |
| *P. aeruginosa* Fisher 4 | + | 9C3 | − | 0 |
| *P. aeruginosa* Fisher 4 | + | 6F11 | + | 0 |
| *P. aeruginosa* Fisher 4 | − | 9C3 | + | 0 |
| *P. aeruginosa* Fisher 4 | + | 9C3 | + | 79% |

[a] − = heat-inactivated (56° C. for 30 min) human complement.
[b] 6F11 = culture supernatant containing an IgM human monoclonal antibody to *Pseudomonas aeruginosa* Fisher type 2.

6. To test the protective characteristics of the 9C3 antibody, animal protection studies were performed with at least one organism from each genus described herein.

The burned mouse model was used for protection experiments with *P. aeruginosa* Fisher 4 and *S. marcescens* 014. For each bacterial challenge, female, outbred Swiss-Webster mice weighing 22–25 gm were divided into three groups of 7 or 8 mice each. An exemplary experiment was performed as follows:

| Group | Bacteria | Antibody |
|---|---|---|
| A | *P. aeruginosa* F4 | 9C3 |
| B | *P. aeruginosa* F4 | 6F11 |
| C | *P. aeruginosa* F2 | 9C3 |

The day before the experiment, each mouse was shaved and treated with a depilatory agent to remove all hair on the back (burn site). On the experiment day, each animal received 0.1 ml in each thigh of an anesthetizing saline solution containing 0.7 ml 0.85% NaCl, 0.2 ml xylazine (20 mg/ml) and 0.1 ml ketamine (100 mg/ml), such that the dosage per mouse was 20 mg/kg zylazine and 180 mg/kg ketamine. The anesthetized mice received a 10% of total body surface area, full-thickness, third degree gas flame burn. Immediately after wound infliction, the mice were injected sub-eschar with 0.5 ml of 4° C. antibody containing spent culture fluid pre-mixed with 5-10 $LD_{50}$'s of bacteria. The bacterial suspension had been prepared from a broth culture in logarithmic phase growth, from which the bacteria were centrifuged, washed twice in PBS, and resuspended to the appropriate concentration in PBS. Animals were observed for a period of ten days. Three to five days post-challenge, all animals in Group B (irrelevant antibody) and Group C (irrelevant organism) were dead. In contrast, those animals that had received the 9C3 (Group A) antibody were all alive and symptom-free (see Table 13).

For the *E. coli* 06 protection studies, healthy Swiss-Webster mice (20–22 gm) were divided into three groups of ten mice each. Each group receiving antibody was injected intravenously with 200 μl of sterile PBS containing 25 μg of purified antibody. Two hours later, all animals were challenged intraperitoneally with 300 μl of live bacteria containing 3 $LD_{50}$'s of their respective bacterial strain (for results, see Table 13).

TABLE 13

| Expt. | Challenge Bacteria | Antibody | Survival/ Challenge | % Survival |
|---|---|---|---|---|
| 1 | P. aeruginosa F4 | 9C3 | 6/7 | 86% |
|   | P. aeruginosa F4 | 6F11(a) | 0/7 | 0 |
|   | P. aeruginosa F2(b) | 9C3 | 0/7 | 0 |
| 2 | E. coli 06 | 9C3 | 6/10 | 60% |
|   | E. coli 06 | 6F11 | 0/10 | 0 |
| 3 | S. marcescens 014 | 9C3 | 8/8 | 100% |
|   | S. marcescens 014 | 6F11 | 0/8 | 0 |

(a)6F11 antibody is specific to *Pseudomonas aeruginosa* Fisher immunotype 2 and serves as negative control antibody.
(b)*P. aeruginosa* F2 is not reactive with the 9C3 antibody and serves as a non-specific control organism.

These data demonstrate that the human monoclonal antibody 9C3 is able to protect mice from lethal challenges with bacteria belonging to three gram-negative genera. The inter-genus cross-reactive human mono- clonal antibody 9C3 was able to afford protection with antibody containing culture supernatant or purified antibody against infection by organisms belonging to the gram-negative genera *E. coli*, *S. marcescens*, and *P. aeruginosa*.

From the foregoing, it will be appreciated that the cell lines of the present invention provide compositions of human monoclonal antibodies and fragments thereof cross-reactive for and cross-protective against various bacterial species, both gram-negative and gram-positive. This allows prophylactic and therapeutic compositions to be more easily developed that can be effective against nosocomial and neonatal infections due to most, if not all, bacterial genera. By combining the antibodies, it is possible to obtain broad protection against a large portion, usually less than all, of the clinically significant bacteria. In addition, the cell lines provide antibodies which find uses in immunoassays and other well-known procedures.

The transformed human cell lines 9B10, 4F10, 4B9, and 7D7, described herein, were deposited in the American Type Culture Collection, 12301 Parklawn Drive, Rockville, Md. 20852, on Jan. 28, 1986, and given the designations CRL 9006, CRL 9007, CRL 9008, and CRL 9009, respectively. The transformed human cell line 9C3, described herein, was deposited in the American Type Culture Collection, 12301 Parklawn Drive, Rockville, Md. 20852, on Oct. 22, 1986, and given the designation CRL 9239.

Although the present invention has been described in some detail by way of illustration and example for purposes of clarity of understanding, it will be obvious that certain changes and modifications may be practiced within the scope of the appended claims.

What is claimed is:

1. A protective human monoclonal antibody or antigen binding fragment thereof which specifically binds to an accessible carbohydrate determinant of outer membrane lipopolysaccharide that immunologically binds a monoclonal antibody produced by a cell line designated ATCC No. CRL 9006, CRL 9007, CRL 9009 or CRL 9239.

2. A composition useful in the prophylactic or therapeutic treatment of bacterial infection, said composition comprising a prophylactic or therapeutic amount of at least two protective human monoclonal antibodies or antigen binding fragments thereof which individually immunologically bind with an accessible carbohydrate determinant of outer membrane lipopolysaccharide shared by serotypes of two or more bacterial species of different genera of Enterobacteriaceae and a plurality of serotypes in at least one of said species, wherein said species comprise *Escherichia coli*, *Serratia marcescens*, *Enterobacter aerogenes*, and *Enterobacter cloacae*.

3. A human monoclonal antibody or binding fragment thereof useful in the treatment of bacterial infection which immunologically binds with an accessible carbohydrate determinant of outer membrane lipopolysaccharide shared by serotypes of at least two different bacterial species and which is protective against infection by bacteria of the serotypes, wherein one of the species is *E. coli*.

4. The human monoclonal antibody of claim 3, wherein the second species which immunologocally binds with the antibody is *Enterobacter cloacae*, *Enterobacter aerogenes*, *Neisseria meningitidis*, *Serratia marcescens*, or *Pseudomonas aeruginosa*.

5. The human monoclonal antibody of claim 4, which immunologically binds with *E. coli*, *S. marcescens*, and *E. aerogenes*.

6. The monoclonal antibody of claim 5 which is obtained from cell line ATCC CRL 9009.

7. The human monoclonal antibody of claim 3, wherein the second and a subsequent species which immunologically bind the antibody are *S. marcescens* and *P. aeruginosa*.

8. The human monoclonal antibody of claim 7 which is obtained from cell line ATCC CRL 9239.

9. A human monoclonal antibody or binding fragment thereof useful in the treatment of bacterial infection which immunologically binds an accessible carbohydrate determinant of outer membrane lipopolysaccharide shared by serotypes of at least two different bacterial species and which is protective against infection by bacteria of the serotypes, wherein one of the species is from the genus Enterobacter.

10. The human monoclonal antibody of claim 9, wherein the second species immunologically binding with the antibody is *E. coli*, *S. marcescens*, or *P. aeruginosa*.

11. A human monoclonal antibody of claim 10 which immunologically binds with *E. aerogenes* and *S. marcescens*.

12. The human monoclonal antibody of claim 11 which is obtained from cell line ATCC CRL 9007.

13. A pharmaceutical composition for the treatment of a bacterial infection in a host which comprises a human monoclonal antibody of claims 3 or 9 and a physiologically acceptable carrier.

14. A human monoclonal antibody useful in the treatment of bacterial infection, having the antigen binding specificity of the antibody produced by the cell line ATCC No. CRL 9009.

15. A pharmaceutical composition for the treatment of bacterial infection in a host which comprises the human monoclonal antibody of claim 14 and a physiologically acceptable carrier.

16. A human monoclonal antibody useful in the treatment of bacterial infection, having the antigen binding specificity of the antibody produced by the cell line ATCC No. CRL 9239.

17. A pharmaceutical composition for the treatment of bacterial infection in a host which comprises the human monoclonal antibody of claim 16 and a physiologically acceptable carrier.

18. A human monoclonal antibody useful in the treatment of bacterial infection, the antibody produced by the cell line ATCC No. CRL 9006.

19. A pharmaceutical composition for the treatment of bacterial infection in a host which comprises the human monoclonal antibody of claim 18 and a physiologically acceptable carrier.

20. A human monoclonal antibody useful in the treatment of bacterial infection, having the antigen binding specificity of the antibody produced by the cell line ATCC No. CRL 9007.

21. A pharmaceutical composition for the treatment of bacterial infection in a host which comprises the human monoclonal antibody of claim 20 and a physiologically acceptable carrier.

22. The human monoclonal antibody of claim 14 which is produced by the cell line ATCC No. CRL 9009.

23. The human monoclonal antibody of claim 16 which is produced by the cell line ATCC No. CRL 9239.

* * * * *